US010011647B2

(12) United States Patent
Murphy et al.

(10) Patent No.: US 10,011,647 B2
(45) Date of Patent: Jul. 3, 2018

(54) IL-33 ANTAGONISTS AND USES THEREOF

(71) Applicant: Regeneron Pharmaceuticals, Inc., Tarrytown, NY (US)

(72) Inventors: Andrew J. Murphy, Croton-on-Hudson, NY (US); Nicholas J. Papadopoulos, LaGrangeville, NY (US); Jamie M. Orengo, Cortlandt Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/463,910

(22) Filed: Mar. 20, 2017

(65) Prior Publication Data
US 2017/0204158 A1 Jul. 20, 2017

Related U.S. Application Data

(62) Division of application No. 14/210,599, filed on Mar. 14, 2014, now Pat. No. 9,637,535.

(60) Provisional application No. 61/787,121, filed on Mar. 15, 2013, provisional application No. 61/819,029, filed on May 3, 2013, provisional application No. 61/913,417, filed on Dec. 9, 2013.

(51) Int. Cl.
*C07K 14/715* (2006.01)
*A61K 39/395* (2006.01)
*A61K 45/06* (2006.01)

(52) U.S. Cl.
CPC ...... *C07K 14/7155* (2013.01); *A61K 39/3955* (2013.01); *A61K 45/06* (2013.01); *C07K 2319/30* (2013.01)

(58) Field of Classification Search
None
See application file for complete search history.

(56) References Cited

U.S. PATENT DOCUMENTS

| 5,576,191 | A  | 11/1996 | Gayle et al. |
|---|---|---|---|
| 8,119,771 | B2 | 2/2012 | Martin |
| 8,187,596 | B1 | 5/2012 | Chackerian et al. |
| 9,453,072 | B2 | 9/2016 | Murphy et al. |
| 2007/0042978 | A1 | 2/2007 | Girard et al. |
| 2007/0087411 | A1 | 4/2007 | Sharma et al. |
| 2009/0041718 | A1 | 2/2009 | Schmitz et al. |
| 2009/0304699 | A1 | 12/2009 | Amatucci et al. |
| 2010/0260705 | A1 | 10/2010 | Martin |
| 2010/0260770 | A1 | 10/2010 | Coyle |
| 2012/0207752 | A1 | 8/2012 | Chackerian et al. |
| 2012/0263709 | A1 | 10/2012 | Rankin et al. |
| 2013/0287777 | A1 | 10/2013 | Duffy et al. |
| 2013/0336980 | A1 | 12/2013 | Duffy et al. |
| 2014/0004107 | A1 | 1/2014 | Smith et al. |
| 2014/0140954 | A1 | 5/2014 | Schmitz et al. |
| 2014/0271642 | A1 | 9/2014 | Murphy et al. |
| 2016/0289322 | A1 | 10/2016 | Fujino et al. |
| 2016/0362487 | A1 | 12/2016 | Murphy et al. |

FOREIGN PATENT DOCUMENTS

| EP | 2069784 A1 | 6/2009 |
|---|---|---|
| EP | 2152740 A1 | 2/2010 |
| EP | 1725261 B1 | 1/2011 |
| EP | 2283860 A2 | 2/2011 |
| EP | 2475388 A1 | 7/2012 |
| WO | WO 05/079844 A2 | 9/2005 |
| WO | WO 08/132709 A1 | 11/2008 |
| WO | WO 08/144610 A1 | 11/2008 |
| WO | WO 09/053098 A1 | 4/2009 |
| WO | WO 11/031600 A1 | 3/2011 |
| WO | WO 14/152195 A1 | 9/2014 |
| WO | WO 14/164959 A2 | 10/2014 |
| WO | WO 15/099175 A1 | 7/2015 |
| WO | WO 15/106080 A2 | 7/2015 |

OTHER PUBLICATIONS

Liew et al, Nature 2016; vol. 16, pp. 676-689.*
"AnaptysBio Announces Development of Novel Anti-IL33 Therapeutic Antibody," AnaptysBio, Inc., 1 page, (2014). [Retrieved from the Internet Jul. 3, 2014: <URL: http://www.anaptysbio.com/anti-1133/>]. (Author Unknown).
Ali et al., "Caspase 3 inactivates biologically active full length interleukin-33 as a classical cytokine but does not prohibit nuclear translocation," Biochemical and Biophysical Research Communications, 391(3):1512-1516, (2010).
Ali, "Characterization of Interleukin-33 and the IL-33 Receptor Complex," Dissertation, pp. 1-126, (2009).
GenBank: Accession No. AEP47229, "Sequence 67 from U.S. Pat. No. 8,008,076," Sep. 30, 2011. [Retrieved from the Internet Mar. 28, 2017: <URL: http://www.ncbi.nlm.nih.gov/protein/AEP47229>].
GenBank: Accession No. AEP47235, "Sequence 111 from U.S. Pat. No. 8,008,076," Sep. 30, 2011. [Retrieved from the Internet Mar. 28, 2017: <URL: http://www.ncbi.nlm.nih.gov/protein/AEP47235>].
GenBank: Accession No. AFD49488, "Sequence 28 from U.S. Pat. No. 8,129,503," Mar. 14, 2012. [Retrieved from the Internet Mar. 28, 2017: <URL: http://www.ncbi.nlm.nih.gov/protein/AFD49488>].

(Continued)

*Primary Examiner* — Bridget E Bunner
*Assistant Examiner* — Fozia Hamud
(74) *Attorney, Agent, or Firm* — Schwabe, Williamson & Wyatt PC; Veronica Mallon

(57) ABSTRACT

The present invention provides interleukin-33 (IL-33) antagonists comprising one or more IL-33-binding domains and one or more multimerizing domains and methods of using the same. According to certain embodiments of the invention, the IL-33-binding domains can comprise an IL-33-binding portion of an ST2 protein and/or an extracellular portion of an IL-1RAcP protein. The IL-33 antagonists of the invention are useful for the treatment of diseases and disorders associated with IL-33 signaling and/or IL-33 cellular expression, such as infectious diseases, inflammatory diseases, allergic diseases and fibrotic diseases.

36 Claims, 1 Drawing Sheet

(56) References Cited

OTHER PUBLICATIONS

GenBank: Accession No. BAC05421, "unnamed protein product [*Homo sapiens*]," Sep. 14, 2016. [Retrieved from the Internet Mar. 28, 2017: <URL: http://www.ncbi.nlm.nih.gov/protein/BAC05421>].
Hayakawa et al., "Soluble ST2 Blocks Interleukin-33 Signaling in Allergic Airway Inflammatioel," Journal of Biological Chemistry, 282(36):26369-26380, (2007).
Hong et al., "The inhibitory function of Fc-ST2 depends on cell type; IL-1RAcP and ST2 are necessary but insufficient for IL-33 activity," Immunol Res, 56:122-130 , (2013).
Hueber et al., "IL-33 induces skin inflammation with mast cell and neutrophil activation," Eur. J. Immunol, 41: 2229-2237, doi: 10.1002/eji.201041360, (2011).
Kim et al., "Beneficial effect of anti-interleukin-33 on the murine model of allergic inflammation of the lower airway.," J Asthma., 49(7):738-743, doi: 10.3109/02770903.2012.702841, (2012).
Kim et al., "Anti-IL-33 antibody has a therapeutic effect in a murine model of allergic rhinitis," Allergy, 8 pages, doi: 10.1111/j.1398-9995.2011.02735.x., (2011).
Li et al., "IL-33 blockade suppresses the development of experimental autoimmune encephalomyelitis in C57BL/6 mice," Journal of Neuroimmunology, 247: 25-31, (2012).
Liew et al., "Disease-associated functions: of IL-33: the new kid in the IL-1 family," Nature Reviews, Immunology, 10(2):103-110 (2010).
Lohning et al., "T1/ST2 is preferentially expressed on murine Th2 cells, independent of interleukin 4, interleukin 5, and interleukin 10, and important for Th2 effector function," Proc. Natl. Acad. Sci. USA, 95(12):6930-0935, (1998).
Oshikawa et al., "Acute eosinophilic pneumonia with increased soluble ST2 in serum and bronchoalveolar lavage fluid," Respiratory Medicine, 95:532-533 (2001).
Oshikawa et al., "Elevated Soluble ST2 Protein Levels in Sera of Patients with Asthma with an Acute Exacerbation," Am J Respir Crit Care Med, 164:277-281, (2001).
Palmer et al., "Interleukin-33 biology with potential insights into human diseases," Nature Reviews, Rheumatology, 7(No):321-329, (2011).
Palmer et al., "The IL-1 receptor accessory protein (AcP) is required for IL-33 signaling and soluble AcP enhances the ability of soluble ST2 to inhibit IL-33," Cytokine, 42(3):358-364, (2008).
Pastorelli et al., "Epithelial-derived IL-33 and its receptor ST2 are dysregulated in ulcerative colitis and in experimental Th1/Th2 driven enteritis," PNAS, 107(17):8017-8022, doi: 10.1073/pnas.0912678107, (2010).
Schmitz et al., "IL-33, an Interleukin-1-like Cytokine that Signals via the IL-1 Receptor-Related Protein ST2 and Induces T Helper Type 2-Associated Cytokines," Immunity, 23:479-490, (2005).
Stevenson et al., "Moving towards a new generation of animal models for asthma and COPD with improved clinical relevance," Pharmacol Ther., 130(2):93-105, Abstract Only, doi: 10.1016/j.pharmthera.2010.10.008, (2011). Epub Nov. 11, 2010.
Stolarski et al., "IL-33 Exacerbates Eosinophil-Mediated Airway Inflammation," J Immunol, 185:3472-3480, doi: 10.4049/jimmunol.1000730, (2010).
Tajima et al., "The Increase in Serum Soluble ST2 Protein Upon Acute Exacerbation of Idiopathic Pulmonary Fibrosis," Chest, 124:1206-1214, (2003).
U.S. Appl. No. 14/205,512, Notice of Allowance dated May 27, 2016.
U.S. Appl. No. 14/205,512, Requirement for Restriction/Election dated Mar. 15, 2016.
U.S. Appl. No. 14/210,599, Non-Final Office Action dated May 23, 2016.
U.S. Appl. No. 14/210,599, Non-Final Office Action dated Sep. 25, 2015.
U.S. Appl. No. 14/210,599, Notice of Allowance dated Dec. 19, 2016.
U.S. Appl. No. 14/210,599, Requirement for Restriction/Election dated Jun. 29, 2015.
WIPO Application No. PCT/US2014/023930, PCT International Preliminary Report on Patentability dated Sep. 24, 2015.
WIPO Application No. PCT/US2014/023930, PCT International Search Report and Written Opinion of the International Searching Authority dated Dec. 12, 2014.
WIPO Application No. PCT/US2014/027058, PCT International Preliminary Report on Patentability dated Sep. 24, 2015.
WIPO Application No. PCT/US2014/027058, PCT International Search Report and Written Opinion of the International Searching Authority dated Jun. 26, 2014.

\* cited by examiner

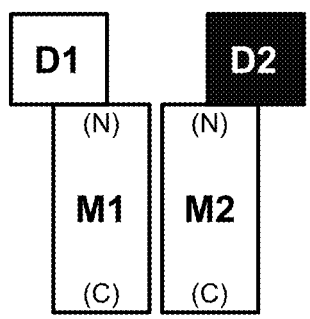
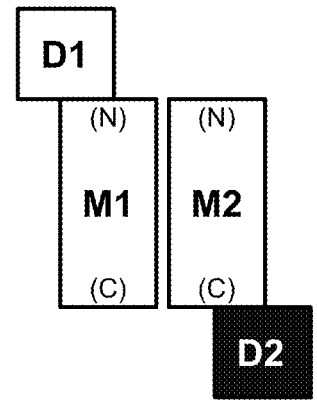
A
B
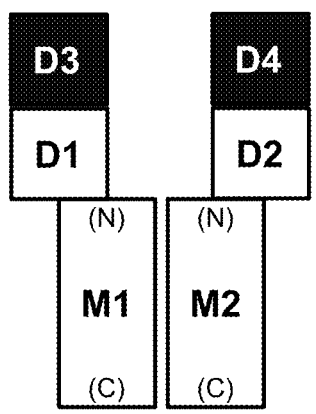
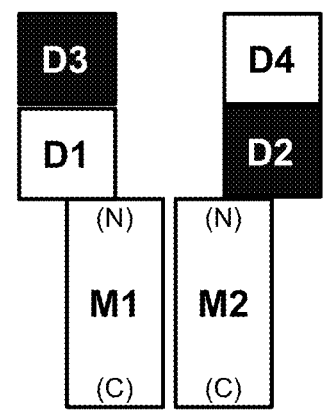
C
D

SEQUENCE LISTING

```
<160> NUMBER OF SEQ ID NOS: 13

<210> SEQ ID NO 1
<211> LENGTH: 537
<212> TYPE: PRT
<213> ORGANISM: Artificial Sequence
<220> FEATURE:
<223> OTHER INFORMATION: synthetic

<400> SEQUENCE: 1
```

-continued

```
Lys Phe Ser Lys Gln Ser Trp Gly Leu Glu Asn Glu Ala Leu Ile Val
 1               5                  10                  15
Arg Cys Pro Arg Gln Gly Lys Pro Ser Tyr Thr Val Asp Trp Tyr Tyr
             20                  25                  30
Ser Gln Thr Asn Lys Ser Ile Pro Thr Gln Glu Arg Asn Arg Val Phe
                 35                  40                  45
Ala Ser Gly Gln Leu Leu Lys Phe Leu Pro Ala Ala Val Ala Asp Ser
         50                  55                  60
Gly Ile Tyr Thr Cys Ile Val Arg Ser Pro Thr Phe Asn Arg Thr Gly
 65                  70                  75                  80
Tyr Ala Asn Val Thr Ile Tyr Lys Lys Gln Ser Asp Cys Asn Val Pro
                 85                  90                  95
Asp Tyr Leu Met Tyr Ser Thr Val Ser Gly Ser Glu Lys Asn Ser Lys
             100                 105                 110
Ile Tyr Cys Pro Thr Ile Asp Leu Tyr Asn Trp Thr Ala Pro Leu Glu
         115                 120                 125
Trp Phe Lys Asn Cys Gln Ala Leu Gln Gly Ser Arg Tyr Arg Ala His
 130                 135                 140
Lys Ser Phe Leu Val Ile Asp Asn Val Met Thr Glu Asp Ala Gly Asp
 145                 150                 155                 160
Tyr Thr Cys Lys Phe Ile His Asn Glu Asn Gly Ala Asn Tyr Ser Val
                 165                 170                 175
Thr Ala Thr Arg Ser Phe Thr Val Lys Asp Glu Gln Gly Phe Ser Leu
             180                 185                 190
Phe Pro Val Ile Gly Ala Pro Ala Gln Asn Glu Ile Lys Glu Val Glu
         195                 200                 205
Ile Gly Lys Asn Ala Asn Leu Thr Cys Ser Ala Cys Phe Gly Lys Gly
 210                 215                 220
Thr Gln Phe Leu Ala Ala Val Leu Trp Gln Leu Asn Gly Thr Lys Ile
 225                 230                 235                 240
Thr Asp Phe Gly Glu Pro Arg Ile Gln Gln Glu Gly Gln Asn Gln
                 245                 250                 255
Ser Phe Ser Asn Gly Leu Ala Cys Leu Asp Met Val Leu Arg Ile Ala
                 260                 265                 270
Asp Val Lys Glu Glu Asp Leu Leu Leu Gln Tyr Asp Cys Leu Ala Leu
             275                 280                 285
Asn Leu His Gly Leu Arg Arg His Thr Val Arg Leu Ser Arg Lys Asn
         290                 295                 300
Pro Ile Asp His His Ser Asp Lys Thr His Thr Cys Pro Pro Cys Pro
 305                 310                 315                 320
Ala Pro Glu Leu Leu Gly Gly Pro Ser Val Phe Leu Phe Pro Pro Lys
                 325                 330                 335
Pro Lys Asp Thr Leu Met Ile Ser Arg Thr Pro Glu Val Thr Cys Val
             340                 345                 350
Val Val Asp Val Ser His Glu Asp Pro Glu Val Lys Phe Asn Trp Tyr
         355                 360                 365
Val Asp Gly Val Glu Val His Asn Ala Lys Thr Lys Pro Arg Glu Glu
 370                 375                 380
Gln Tyr Asn Ser Thr Tyr Arg Val Val Ser Val Leu Thr Val Leu His
 385                 390                 395                 400
Gln Asp Trp Leu Asn Gly Lys Glu Tyr Lys Cys Lys Val Ser Asn Lys
                 405                 410                 415
```

```
Ala Leu Pro Ala Pro Ile Glu Lys Thr Ile Ser Lys Ala Lys Gly Gln
            420                 425                 430

Pro Arg Glu Pro Gln Val Tyr Thr Leu Pro Pro Ser Arg Asp Glu Leu
        435                 440                 445

Thr Lys Asn Gln Val Ser Leu Thr Cys Leu Val Lys Gly Phe Tyr Pro
    450                 455                 460

Ser Asp Ile Ala Val Glu Trp Glu Ser Asn Gly Gln Pro Glu Asn Asn
465                 470                 475                 480

Tyr Lys Thr Thr Pro Pro Val Leu Asp Ser Asp Gly Ser Phe Phe Leu
                485                 490                 495

Tyr Ser Lys Leu Thr Val Asp Lys Ser Arg Trp Gln Gln Gly Asn Val
            500                 505                 510

Phe Ser Cys Ser Val Met His Glu Ala Leu His Asn His Tyr Thr Gln
        515                 520                 525

Lys Ser Leu Ser Leu Ser Pro Gly Lys
    530                 535
```

<210> SEQ ID NO 2
<211> LENGTH: 543
<212> TYPE: PRT
<213> ORGANISM: Artificial Sequence
<220> FEATURE:
<223> OTHER INFORMATION: synthetic

<400> SEQUENCE: 2

```
Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Ala Val Ala Asp Ser
    50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
        115                 120                 125

Trp Phe Lys Asn Cys Gln Ala Leu Gln Gly Ser Arg Tyr Arg Ala His
    130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
            180                 185                 190

Phe Pro Val Ile Gly Ala Pro Ala Gln Asn Glu Ile Lys Glu Val Glu
        195                 200                 205

Ile Gly Lys Asn Ala Asn Leu Thr Cys Ser Ala Cys Phe Gly Lys Gly
    210                 215                 220

Thr Gln Phe Leu Ala Ala Val Leu Trp Gln Leu Asn Gly Thr Lys Ile
225                 230                 235                 240
```

```
Thr Asp Phe Gly Glu Pro Arg Ile Gln Gln Glu Gly Gln Asn Gln
                245                 250                 255

Ser Phe Ser Asn Gly Leu Ala Cys Leu Asp Met Val Leu Arg Ile Ala
            260                 265                 270

Asp Val Lys Glu Glu Asp Leu Leu Gln Tyr Asp Cys Leu Ala Leu
        275                 280                 285

Asn Leu His Gly Leu Arg Arg His Thr Val Arg Leu Ser Arg Lys Asn
    290                 295                 300

Pro Ile Asp His His Ser Glu Pro Arg Gly Pro Thr Ile Lys Pro Cys
305                 310                 315                 320

Pro Pro Cys Lys Cys Pro Ala Pro Asn Leu Leu Gly Gly Pro Ser Val
                325                 330                 335

Phe Ile Phe Pro Pro Lys Ile Lys Asp Val Leu Met Ile Ser Leu Ser
            340                 345                 350

Pro Ile Val Thr Cys Val Val Val Asp Val Ser Glu Asp Asp Pro Asp
        355                 360                 365

Val Gln Ile Ser Trp Phe Val Asn Asn Val Glu Val His Thr Ala Gln
    370                 375                 380

Thr Gln Thr His Arg Glu Asp Tyr Asn Ser Thr Leu Arg Val Val Ser
385                 390                 395                 400

Ala Leu Pro Ile Gln His Gln Asp Trp Met Ser Gly Lys Glu Phe Lys
                405                 410                 415

Cys Lys Val Asn Asn Lys Asp Leu Pro Ala Pro Ile Glu Arg Thr Ile
            420                 425                 430

Ser Lys Pro Lys Gly Ser Val Arg Ala Pro Gln Val Tyr Val Leu Pro
        435                 440                 445

Pro Pro Glu Glu Glu Met Thr Lys Lys Gln Val Thr Leu Thr Cys Met
    450                 455                 460

Val Thr Asp Phe Met Pro Glu Asp Ile Tyr Val Glu Trp Thr Asn Asn
465                 470                 475                 480

Gly Lys Thr Glu Leu Asn Tyr Lys Asn Thr Glu Pro Val Leu Asp Ser
                485                 490                 495

Asp Gly Ser Tyr Phe Met Tyr Ser Lys Leu Arg Val Glu Lys Lys Asn
            500                 505                 510

Trp Val Glu Arg Asn Ser Tyr Ser Cys Ser Val Val His Glu Gly Leu
        515                 520                 525

His Asn His His Thr Thr Lys Ser Phe Ser Arg Thr Pro Gly Lys
    530                 535                 540

<210> SEQ ID NO 3
<211> LENGTH: 884
<212> TYPE: PRT
<213> ORGANISM: Artificial Sequence
<220> FEATURE:
<223> OTHER INFORMATION: synthetic

<400> SEQUENCE: 3

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Ala Val Ala Asp Ser
    50                  55                  60
```

-continued

```
Gly Ile Tyr Thr Cys Ile Val Arg Ser Pro Thr Phe Asn Arg Thr Gly
 65                  70                  75                  80

Tyr Ala Asn Val Thr Ile Tyr Lys Lys Gln Ser Asp Cys Asn Val Pro
                 85                  90                  95

Asp Tyr Leu Met Tyr Ser Thr Val Ser Gly Ser Glu Lys Asn Ser Lys
                100                 105                 110

Ile Tyr Cys Pro Thr Ile Asp Leu Tyr Asn Trp Thr Ala Pro Leu Glu
            115                 120                 125

Trp Phe Lys Asn Cys Gln Ala Leu Gln Gly Ser Arg Tyr Arg Ala His
        130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
                180                 185                 190

Phe Pro Val Ile Gly Ala Pro Ala Gln Asn Glu Ile Lys Glu Val Glu
            195                 200                 205

Ile Gly Lys Asn Ala Asn Leu Thr Cys Ser Ala Cys Phe Gly Lys Gly
        210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Gly Gln Asn Gln
                245                 250                 255

Ser Phe Ser Asn Gly Leu Ala Cys Leu Asp Met Val Leu Arg Ile Ala
                260                 265                 270

Asp Val Lys Glu Glu Asp Leu Leu Leu Gln Tyr Asp Cys Leu Ala Leu
            275                 280                 285

Asn Leu His Gly Leu Arg Arg His Thr Val Arg Leu Ser Arg Lys Asn
        290                 295                 300

Pro Ile Asp His His Ser Ser Glu Arg Cys Asp Asp Trp Gly Leu Asp
305                 310                 315                 320

Thr Met Arg Gln Ile Gln Val Phe Glu Asp Glu Pro Ala Arg Ile Lys
                325                 330                 335

Cys Pro Leu Phe Glu His Phe Leu Lys Phe Asn Tyr Ser Thr Ala His
            340                 345                 350

Ser Ala Gly Leu Thr Leu Ile Trp Tyr Trp Thr Arg Gln Asp Arg Asp
        355                 360                 365

Leu Glu Glu Pro Ile Asn Phe Arg Leu Pro Glu Asn Arg Ile Ser Lys
370                 375                 380

Glu Lys Asp Val Leu Trp Phe Arg Pro Thr Leu Leu Asn Asp Thr Gly
385                 390                 395                 400

Asn Tyr Thr Cys Met Leu Arg Asn Thr Thr Tyr Cys Ser Lys Val Ala
                405                 410                 415

Phe Pro Leu Glu Val Val Gln Lys Asp Ser Cys Phe Asn Ser Pro Met
            420                 425                 430

Lys Leu Pro Val His Lys Leu Tyr Ile Glu Tyr Gly Ile Gln Arg Ile
        435                 440                 445

Thr Cys Pro Asn Val Asp Gly Tyr Phe Pro Ser Ser Val Lys Pro Thr
450                 455                 460

Ile Thr Trp Tyr Met Gly Cys Tyr Lys Ile Gln Asn Phe Asn Asn Val
465                 470                 475                 480

Ile Pro Glu Gly Met Asn Leu Ser Phe Leu Ile Ala Leu Ile Ser Asn
```

```
            485                 490                 495
Asn Gly Asn Tyr Thr Cys Val Val Thr Tyr Pro Glu Asn Gly Arg Thr
            500                 505                 510

Phe His Leu Thr Arg Thr Leu Thr Val Lys Val Val Gly Ser Pro Lys
            515                 520                 525

Asn Ala Val Pro Pro Val Ile His Ser Pro Asn Asp His Val Val Tyr
        530                 535                 540

Glu Lys Glu Pro Gly Glu Leu Leu Ile Pro Cys Thr Val Tyr Phe
545                 550                 555                 560

Ser Phe Leu Met Asp Ser Arg Asn Glu Val Trp Trp Thr Ile Asp Gly
                565                 570                 575

Lys Lys Pro Asp Asp Ile Thr Ile Asp Val Thr Ile Asn Glu Ser Ile
                580                 585                 590

Ser His Ser Arg Thr Glu Asp Glu Thr Arg Thr Gln Ile Leu Ser Ile
                595                 600                 605

Lys Lys Val Thr Ser Glu Asp Leu Lys Arg Ser Tyr Val Cys His Ala
                610                 615                 620

Arg Ser Ala Lys Gly Glu Val Ala Lys Ala Ala Lys Val Lys Gln Lys
625                 630                 635                 640

Val Pro Ala Pro Arg Tyr Thr Val Glu Ser Gly Glu Pro Arg Gly Pro
                645                 650                 655

Thr Ile Lys Pro Cys Pro Pro Cys Lys Cys Pro Ala Pro Asn Leu Leu
                660                 665                 670

Gly Gly Pro Ser Val Phe Ile Phe Pro Pro Lys Ile Lys Asp Val Leu
                675                 680                 685

Met Ile Ser Leu Ser Pro Ile Val Thr Cys Val Val Val Asp Val Ser
        690                 695                 700

Glu Asp Asp Pro Asp Val Gln Ile Ser Trp Phe Val Asn Asn Val Glu
705                 710                 715                 720

Val His Thr Ala Gln Thr Gln Thr His Arg Glu Asp Tyr Asn Ser Thr
                725                 730                 735

Leu Arg Val Val Ser Ala Leu Pro Ile Gln His Gln Asp Trp Met Ser
                740                 745                 750

Gly Lys Glu Phe Lys Cys Lys Val Asn Asn Lys Asp Leu Pro Ala Pro
                755                 760                 765

Ile Glu Arg Thr Ile Ser Lys Pro Lys Gly Ser Val Arg Ala Pro Gln
                770                 775                 780

Val Tyr Val Leu Pro Pro Pro Glu Glu Glu Met Thr Lys Lys Gln Val
785                 790                 795                 800

Thr Leu Thr Cys Met Val Thr Asp Phe Met Pro Glu Asp Ile Tyr Val
                805                 810                 815

Glu Trp Thr Asn Asn Gly Lys Thr Glu Leu Asn Tyr Lys Asn Thr Glu
                820                 825                 830

Pro Val Leu Asp Ser Asp Gly Ser Tyr Phe Met Tyr Ser Lys Leu Arg
                835                 840                 845

Val Glu Lys Lys Asn Trp Val Glu Arg Asn Ser Tyr Ser Cys Ser Val
                850                 855                 860

Val His Glu Gly Leu His Asn His His Thr Thr Lys Ser Phe Ser Arg
865                 870                 875                 880

Thr Pro Gly Lys

<210> SEQ ID NO 4
<211> LENGTH: 880
```

<212> TYPE: PRT
<213> ORGANISM: Artificial Sequence
<220> FEATURE:
<223> OTHER INFORMATION: synthetic

<400> SEQUENCE: 4

Ser Lys Ser Ser Trp Gly Leu Glu Asn Glu Ala Leu Ile Val Arg Cys
1               5                   10                  15

Pro Gln Arg Gly Arg Ser Thr Tyr Pro Val Glu Trp Tyr Tyr Ser Asp
                20                  25                  30

Thr Asn Glu Ser Ile Pro Thr Gln Lys Arg Asn Arg Ile Phe Val Ser
            35                  40                  45

Arg Asp Arg Leu Lys Phe Leu Pro Ala Arg Val Glu Asp Ser Gly Ile
        50                  55                  60

Tyr Ala Cys Val Ile Arg Ser Pro Asn Leu Asn Lys Thr Gly Tyr Leu
65                  70                  75                  80

Asn Val Thr Ile His Lys Lys Pro Pro Ser Cys Asn Ile Pro Asp Tyr
                85                  90                  95

Leu Met Tyr Ser Thr Val Arg Gly Ser Asp Lys Asn Phe Lys Ile Thr
            100                 105                 110

Cys Pro Thr Ile Asp Leu Tyr Asn Trp Thr Ala Pro Val Gln Trp Phe
        115                 120                 125

Lys Asn Cys Lys Ala Leu Gln Glu Pro Arg Phe Arg Ala His Arg Ser
130                 135                 140

Tyr Leu Phe Ile Asp Asn Val Thr His Asp Asp Glu Gly Asp Tyr Thr
145                 150                 155                 160

Cys Gln Phe Thr His Ala Glu Asn Gly Thr Asn Tyr Ile Val Thr Ala
                165                 170                 175

Thr Arg Ser Phe Thr Val Glu Glu Lys Gly Phe Ser Met Phe Pro Val
            180                 185                 190

Ile Thr Asn Pro Pro Tyr Asn His Thr Met Glu Val Glu Ile Gly Lys
        195                 200                 205

Pro Ala Ser Ile Ala Cys Ser Ala Cys Phe Gly Lys Gly Ser His Phe
210                 215                 220

Leu Ala Asp Val Leu Trp Gln Ile Asn Lys Thr Val Val Gly Asn Phe
225                 230                 235                 240

Gly Glu Ala Arg Ile Gln Glu Glu Gly Arg Asn Glu Ser Ser Ser
                245                 250                 255

Asn Asp Met Asp Cys Leu Thr Ser Val Leu Arg Ile Thr Gly Val Thr
            260                 265                 270

Glu Lys Asp Leu Ser Leu Glu Tyr Asp Cys Leu Ala Leu Asn Leu His
        275                 280                 285

Gly Met Ile Arg His Thr Ile Arg Leu Arg Arg Lys Gln Pro Ile Asp
290                 295                 300

His Arg Ser Glu Arg Cys Asp Asp Trp Gly Leu Asp Thr Met Arg Gln
305                 310                 315                 320

Ile Gln Val Phe Glu Asp Glu Pro Ala Arg Ile Lys Cys Pro Leu Phe
                325                 330                 335

Glu His Phe Leu Lys Tyr Asn Tyr Ser Thr Ala His Ser Ser Gly Leu
            340                 345                 350

Thr Leu Ile Trp Tyr Trp Thr Arg Gln Asp Arg Asp Leu Glu Glu Pro
        355                 360                 365

Ile Asn Phe Arg Leu Pro Glu Asn Arg Ile Ser Lys Glu Lys Asp Val
370                 375                 380

-continued

```
Leu Trp Phe Arg Pro Thr Leu Leu Asn Asp Thr Gly Asn Tyr Thr Cys
385                 390                 395                 400

Met Leu Arg Asn Thr Thr Tyr Cys Ser Lys Val Ala Phe Pro Leu Glu
            405                 410                 415

Val Val Gln Lys Asp Ser Cys Phe Asn Ser Ala Met Arg Phe Pro Val
        420                 425                 430

His Lys Met Tyr Ile Glu His Gly Ile His Lys Ile Thr Cys Pro Asn
    435                 440                 445

Val Asp Gly Tyr Phe Pro Ser Ser Val Lys Pro Ser Val Thr Trp Tyr
450                 455                 460

Lys Gly Cys Thr Glu Ile Val Asp Phe His Asn Val Leu Pro Glu Gly
465                 470                 475                 480

Met Asn Leu Ser Phe Phe Ile Pro Leu Val Ser Asn Asn Gly Asn Tyr
            485                 490                 495

Thr Cys Val Val Thr Tyr Pro Glu Asn Gly Arg Leu Phe His Leu Thr
        500                 505                 510

Arg Thr Val Thr Val Lys Val Val Gly Ser Pro Lys Asp Ala Leu Pro
    515                 520                 525

Pro Gln Ile Tyr Ser Pro Asn Asp Arg Val Val Tyr Glu Lys Glu Pro
530                 535                 540

Gly Glu Glu Leu Val Ile Pro Cys Lys Val Tyr Phe Ser Phe Ile Met
545                 550                 555                 560

Asp Ser His Asn Glu Val Trp Trp Thr Ile Asp Gly Lys Lys Pro Asp
            565                 570                 575

Asp Val Thr Val Asp Ile Thr Ile Asn Glu Ser Val Ser Tyr Ser Ser
        580                 585                 590

Thr Glu Asp Glu Thr Arg Thr Gln Ile Leu Ser Ile Lys Lys Val Thr
    595                 600                 605

Pro Glu Asp Leu Arg Arg Asn Tyr Val Cys His Ala Arg Asn Thr Lys
610                 615                 620

Gly Glu Ala Glu Gln Ala Ala Lys Val Lys Gln Lys Val Ile Pro Pro
625                 630                 635                 640

Arg Tyr Thr Val Glu Ser Gly Glu Pro Arg Gly Pro Thr Ile Lys Pro
            645                 650                 655

Cys Pro Pro Cys Lys Cys Pro Ala Pro Asn Leu Leu Gly Gly Pro Ser
        660                 665                 670

Val Phe Ile Phe Pro Pro Lys Ile Lys Asp Val Leu Met Ile Ser Leu
    675                 680                 685

Ser Pro Ile Val Thr Cys Val Val Val Asp Val Ser Glu Asp Asp Pro
690                 695                 700

Asp Val Gln Ile Ser Trp Phe Val Asn Asn Val Glu Val His Thr Ala
705                 710                 715                 720

Gln Thr Gln Thr His Arg Glu Asp Tyr Asn Ser Thr Leu Arg Val Val
            725                 730                 735

Ser Ala Leu Pro Ile Gln His Gln Asp Trp Met Ser Gly Lys Glu Phe
        740                 745                 750

Lys Cys Lys Val Asn Asn Lys Asp Leu Pro Ala Pro Ile Glu Arg Thr
    755                 760                 765

Ile Ser Lys Pro Lys Gly Ser Val Arg Ala Pro Gln Val Tyr Val Leu
770                 775                 780

Pro Pro Pro Glu Glu Glu Met Thr Lys Lys Gln Val Thr Leu Thr Cys
785                 790                 795                 800

Met Val Thr Asp Phe Met Pro Glu Asp Ile Tyr Val Glu Trp Thr Asn
```

```
            805                 810                 815
Asn Gly Lys Thr Glu Leu Asn Tyr Lys Asn Thr Glu Pro Val Leu Asp
            820                 825                 830

Ser Asp Gly Ser Tyr Phe Met Tyr Ser Lys Leu Arg Val Glu Lys Lys
            835                 840                 845

Asn Trp Val Glu Arg Asn Ser Tyr Ser Cys Ser Val Val His Glu Gly
            850                 855                 860

Leu His Asn His His Thr Thr Lys Ser Phe Ser Arg Thr Pro Gly Lys
865                 870                 875                 880

<210> SEQ ID NO 5
<211> LENGTH: 310
<212> TYPE: PRT
<213> ORGANISM: Artificial Sequence
<220> FEATURE:
<223> OTHER INFORMATION: synthetic

<400> SEQUENCE: 5

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Ala Val Ala Asp Ser
    50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
        115                 120                 125

Trp Phe Lys Asn Cys Gln Ala Leu Gln Gly Ser Arg Tyr Arg Ala His
    130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
            180                 185                 190

Phe Pro Val Ile Gly Ala Pro Ala Gln Asn Glu Ile Lys Glu Val Glu
        195                 200                 205

Ile Gly Lys Asn Ala Asn Leu Thr Cys Ser Ala Cys Phe Gly Lys Gly
    210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Glu Gly Gln Asn Gln
                245                 250                 255

Ser Phe Ser Asn Gly Leu Ala Cys Leu Asp Met Val Leu Arg Ile Ala
            260                 265                 270

Asp Val Lys Glu Glu Asp Leu Leu Leu Gln Tyr Asp Cys Leu Ala Leu
        275                 280                 285

Asn Leu His Gly Leu Arg Arg His Thr Val Arg Leu Ser Arg Lys Asn
```

```
                290                 295                 300

Pro Ile Asp His His Ser
305                 310

<210> SEQ ID NO 6
<211> LENGTH: 306
<212> TYPE: PRT
<213> ORGANISM: Artificial Sequence
<220> FEATURE:
<223> OTHER INFORMATION: synthetic

<400> SEQUENCE: 6

Ser Lys Ser Ser Trp Gly Leu Glu Asn Glu Ala Leu Ile Val Arg Cys
  1               5                  10                  15

Pro Gln Arg Gly Arg Ser Thr Tyr Pro Val Glu Trp Tyr Tyr Ser Asp
                 20                  25                  30

Thr Asn Glu Ser Ile Pro Thr Gln Lys Arg Asn Arg Ile Phe Val Ser
             35                  40                  45

Arg Asp Arg Leu Lys Phe Leu Pro Ala Arg Val Glu Asp Ser Gly Ile
         50                  55                  60

Tyr Ala Cys Val Ile Arg Ser Pro Asn Leu Asn Lys Thr Gly Tyr Leu
 65                  70                  75                  80

Asn Val Thr Ile His Lys Lys Pro Pro Ser Cys Asn Ile Pro Asp Tyr
                 85                  90                  95

Leu Met Tyr Ser Thr Val Arg Gly Ser Asp Lys Asn Phe Lys Ile Thr
            100                 105                 110

Cys Pro Thr Ile Asp Leu Tyr Asn Trp Thr Ala Pro Val Gln Trp Phe
        115                 120                 125

Lys Asn Cys Lys Ala Leu Gln Glu Pro Arg Phe Arg Ala His Arg Ser
    130                 135                 140

Tyr Leu Phe Ile Asp Asn Val Thr His Asp Asp Glu Gly Asp Tyr Thr
145                 150                 155                 160

Cys Gln Phe Thr His Ala Glu Asn Gly Thr Asn Tyr Ile Val Thr Ala
                165                 170                 175

Thr Arg Ser Phe Thr Val Glu Glu Lys Gly Phe Ser Met Phe Pro Val
            180                 185                 190

Ile Thr Asn Pro Pro Tyr Asn His Thr Met Glu Val Glu Ile Gly Lys
        195                 200                 205

Pro Ala Ser Ile Ala Cys Ser Ala Cys Phe Gly Lys Gly Ser His Phe
    210                 215                 220

Leu Ala Asp Val Leu Trp Gln Ile Asn Lys Thr Val Val Gly Asn Phe
225                 230                 235                 240

Gly Glu Ala Arg Ile Gln Glu Glu Gly Arg Asn Glu Ser Ser Ser
                245                 250                 255

Asn Asp Met Asp Cys Leu Thr Ser Val Leu Arg Ile Thr Gly Val Thr
            260                 265                 270

Glu Lys Asp Leu Ser Leu Glu Tyr Asp Cys Leu Ala Leu Asn Leu His
        275                 280                 285

Gly Met Ile Arg His Thr Ile Arg Leu Arg Arg Lys Gln Pro Ile Asp
    290                 295                 300

His Arg
305

<210> SEQ ID NO 7
<211> LENGTH: 339
<212> TYPE: PRT
```

<213> ORGANISM: Artificial Sequence
<220> FEATURE:
<223> OTHER INFORMATION: synthetic

<400> SEQUENCE: 7

```
Ser Glu Arg Cys Asp Asp Trp Gly Leu Asp Thr Met Arg Gln Ile Gln
 1               5                  10                  15

Val Phe Glu Asp Glu Pro Ala Arg Ile Lys Cys Pro Leu Phe Glu His
             20                  25                  30

Phe Leu Lys Phe Asn Tyr Ser Thr Ala His Ser Ala Gly Leu Thr Leu
         35                  40                  45

Ile Trp Tyr Trp Thr Arg Gln Asp Arg Asp Leu Glu Glu Pro Ile Asn
 50                  55                  60

Phe Arg Leu Pro Glu Asn Arg Ile Ser Lys Glu Lys Asp Val Leu Trp
 65                  70                  75                  80

Phe Arg Pro Thr Leu Leu Asn Asp Thr Gly Asn Tyr Thr Cys Met Leu
                 85                  90                  95

Arg Asn Thr Thr Tyr Cys Ser Lys Val Ala Phe Pro Leu Glu Val Val
             100                 105                 110

Gln Lys Asp Ser Cys Phe Asn Ser Pro Met Lys Leu Pro Val His Lys
         115                 120                 125

Leu Tyr Ile Glu Tyr Gly Ile Gln Arg Ile Thr Cys Pro Asn Val Asp
130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
    210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Thr Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
    290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Val Pro Ala Pro Arg Tyr
                325                 330                 335

Thr Val Glu
```

<210> SEQ ID NO 8
<211> LENGTH: 339
<212> TYPE: PRT
<213> ORGANISM: Artificial Sequence
<220> FEATURE:
<223> OTHER INFORMATION: synthetic

<400> SEQUENCE: 8

```
Ser Glu Arg Cys Asp Asp Trp Gly Leu Asp Thr Met Arg Gln Ile Gln
 1               5                  10                  15

Val Phe Glu Asp Glu Pro Ala Arg Ile Lys Cys Pro Leu Phe Glu His
            20                  25                  30

Phe Leu Lys Tyr Asn Tyr Ser Thr Ala His Ser Ser Gly Leu Thr Leu
        35                  40                  45

Ile Trp Tyr Trp Thr Arg Gln Asp Arg Asp Leu Glu Glu Pro Ile Asn
 50                  55                  60

Phe Arg Leu Pro Glu Asn Arg Ile Ser Lys Glu Lys Asp Val Leu Trp
 65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Ala Met Arg Phe Pro Val His Lys
        115                 120                 125

Met Tyr Ile Glu His Gly Ile His Lys Ile Thr Cys Pro Asn Val Asp
130                 135                 140

Gly Tyr Phe Pro Ser Ser Val Lys Pro Ser Val Thr Trp Tyr Lys Gly
145                 150                 155                 160

Cys Thr Glu Ile Val Asp Phe His Asn Val Leu Pro Glu Gly Met Asn
                165                 170                 175

Leu Ser Phe Phe Ile Pro Leu Val Ser Asn Asn Gly Asn Tyr Thr Cys
            180                 185                 190

Val Val Thr Tyr Pro Glu Asn Gly Arg Leu Phe His Leu Thr Arg Thr
        195                 200                 205

Val Thr Val Lys Val Val Gly Ser Pro Lys Asp Ala Leu Pro Pro Gln
210                 215                 220

Ile Tyr Ser Pro Asn Asp Arg Val Val Tyr Glu Lys Glu Pro Gly Glu
225                 230                 235                 240

Glu Leu Val Ile Pro Cys Lys Val Tyr Phe Ser Phe Ile Met Asp Ser
                245                 250                 255

His Asn Glu Val Trp Trp Thr Ile Asp Gly Lys Lys Pro Asp Asp Val
            260                 265                 270

Thr Val Asp Ile Thr Ile Asn Glu Ser Val Ser Tyr Ser Ser Thr Glu
        275                 280                 285

Asp Glu Thr Arg Thr Gln Ile Leu Ser Ile Lys Lys Val Thr Pro Glu
290                 295                 300

Asp Leu Arg Arg Asn Tyr Val Cys His Ala Arg Asn Thr Lys Gly Glu
305                 310                 315                 320

Ala Glu Gln Ala Ala Lys Val Lys Gln Lys Val Ile Pro Pro Arg Tyr
                325                 330                 335

Thr Val Glu
```

<210> SEQ ID NO 9
<211> LENGTH: 227
<212> TYPE: PRT
<213> ORGANISM: Artificial Sequence
<220> FEATURE:
<223> OTHER INFORMATION: synthetic

<400> SEQUENCE: 9

```
Asp Lys Thr His Thr Cys Pro Pro Cys Pro Ala Pro Glu Leu Leu Gly
 1               5                  10                  15
```

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 10
<211> LENGTH: 233
<212> TYPE: PRT
<213> ORGANISM: Artificial Sequence
<220> FEATURE:
<223> OTHER INFORMATION: synthetic

<400> SEQUENCE: 10

Glu Pro Arg Gly Pro Thr Ile Lys Pro Cys Pro Pro Cys Lys Cys Pro
 1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
 50                  55                  60

Val Asn Asn Val Glu Val His Thr Ala Gln Thr Gln Thr His Arg Glu
 65                  70                  75                  80

Asp Tyr Asn Ser Thr Leu Arg Val Val Ser Ala Leu Pro Ile Gln His
                 85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
130                 135                 140

```
Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230
```

<210> SEQ ID NO 11
<211> LENGTH: 167
<212> TYPE: PRT
<213> ORGANISM: Artificial Sequence
<220> FEATURE:
<223> OTHER INFORMATION: synthetic

<400> SEQUENCE: 11

```
Ser Ile Thr Gly Ile Ser Pro Ile Thr Glu Ser Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Lys Lys Lys Asp Lys Val
        35                  40                  45

Leu Leu Ser Tyr Tyr Glu Ser Gln His Pro Ser Ser Glu Ser Gly Asp
    50                  55                  60

Gly Val Asp Gly Lys Met Leu Met Val Thr Leu Ser Pro Thr Lys Asp
65                  70                  75                  80

Phe Trp Leu Gln Ala Asn Asn Lys Glu His Ser Val Glu Leu His Lys
                85                  90                  95

Cys Glu Lys Pro Leu Pro Asp Gln Ala Phe Phe Val Leu His Asn Arg
            100                 105                 110

Ser Phe Asn Cys Val Ser Phe Glu Cys Lys Thr Asp Pro Gly Val Phe
        115                 120                 125

Ile Gly Val Lys Asp Asn His Leu Ala Leu Ile Lys Val Asp Tyr Ser
    130                 135                 140

Glu Asn Leu Gly Ser Glu Asn Ile Leu Phe Lys Leu Ser Glu Ile Leu
145                 150                 155                 160

Glu His His His His His His
                165
```

<210> SEQ ID NO 12
<211> LENGTH: 167
<212> TYPE: PRT
<213> ORGANISM: Artificial Sequence
<220> FEATURE:
<223> OTHER INFORMATION: synthetic
<220> FEATURE:
<223> OTHER INFORMATION: aa 1-159: M.fascicularis IL-33 (S112-E269 of
      accession number EHH57404.1 with an extra I after
      E269)
<220> FEATURE:
<223> OTHER INFORMATION: aa 160-161: linker
<220> FEATURE:
<223> OTHER INFORMATION: aa 162-167: hexahistidine tag

<400> SEQUENCE: 12

Ser Ile Thr Gly Ile Ser Pro Ile Thr Glu Ser Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Lys Lys Lys Asp Lys Val
        35                  40                  45

Leu Leu Ser Tyr Tyr Glu Ser Gln His Pro Ser Ser Glu Ser Gly Asp
50                  55                  60

Gly Val Asp Gly Lys Met Leu Met Val Thr Leu Ser Pro Thr Lys Asp
65                  70                  75                  80

Phe Trp Leu Gln Ala Asn Asn Lys Glu His Ser Val Glu Leu His Lys
                85                  90                  95

Cys Glu Lys Pro Leu Pro Asp Gln Ala Phe Phe Val Leu His Asn Arg
            100                 105                 110

Ser Phe Asn Cys Val Ser Phe Glu Cys Lys Thr Asp Pro Gly Val Phe
        115                 120                 125

Ile Gly Val Lys Asp Asn His Leu Ala Leu Ile Lys Val Asp Tyr Ser
130                 135                 140

Glu Asn Leu Gly Ser Glu Asn Ile Leu Phe Lys Leu Ser Glu Ile Leu
145                 150                 155                 160

Glu His His His His His His
                165

<210> SEQ ID NO 13
<211> LENGTH: 876
<212> TYPE: PRT
<213> ORGANISM: Artificial Sequence
<220> FEATURE:
<223> OTHER INFORMATION: synthetic
<220> FEATURE:
<223> OTHER INFORMATION: aa 1-310: Human ST2 (K19-S328 of accession
      number NP_057316.3)
<220> FEATURE:
<223> OTHER INFORMATION: aa 311-649: Human IL1RacP (S21-E359 of
      accession number Q9NPH3)
<220> FEATURE:
<223> OTHER INFORMATION: aa 650-876: hFc tag (D104-K330 of accession
      number P01857)

<400> SEQUENCE: 13

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Ala Val Ala Asp Ser
50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
        115                 120                 125

Trp Phe Lys Asn Cys Gln Ala Leu Gln Gly Ser Arg Tyr Arg Ala His
130                 135                 140

-continued

```
Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
            165                 170                 175

Thr Ala Thr Arg Ser Phe Thr Val Lys Asp Glu Gln Gly Phe Ser Leu
        180                 185                 190

Phe Pro Val Ile Gly Ala Pro Ala Gln Asn Glu Ile Lys Glu Val Glu
    195                 200                 205

Ile Gly Lys Asn Ala Asn Leu Thr Cys Ser Ala Cys Phe Gly Lys Gly
210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Glu Gly Gln Asn Gln
                245                 250                 255

Ser Phe Ser Asn Gly Leu Ala Cys Leu Asp Met Val Leu Arg Ile Ala
            260                 265                 270

Asp Val Lys Glu Glu Asp Leu Leu Gln Tyr Asp Cys Leu Ala Leu
        275                 280                 285

Asn Leu His Gly Leu Arg Arg His Thr Val Arg Leu Ser Arg Lys Asn
    290                 295                 300

Pro Ile Asp His His Ser Ser Glu Arg Cys Asp Asp Trp Gly Leu Asp
305                 310                 315                 320

Thr Met Arg Gln Ile Gln Val Phe Glu Asp Glu Pro Ala Arg Ile Lys
                325                 330                 335

Cys Pro Leu Phe Glu His Phe Leu Lys Phe Asn Tyr Ser Thr Ala His
            340                 345                 350

Ser Ala Gly Leu Thr Leu Ile Trp Tyr Trp Thr Arg Gln Asp Arg Asp
        355                 360                 365

Leu Glu Glu Pro Ile Asn Phe Arg Leu Pro Glu Asn Arg Ile Ser Lys
    370                 375                 380

Glu Lys Asp Val Leu Trp Phe Arg Pro Thr Leu Leu Asn Asp Thr Gly
385                 390                 395                 400

Asn Tyr Thr Cys Met Leu Arg Asn Thr Thr Tyr Cys Ser Lys Val Ala
                405                 410                 415

Phe Pro Leu Glu Val Val Gln Lys Asp Ser Cys Phe Asn Ser Pro Met
            420                 425                 430

Lys Leu Pro Val His Lys Leu Tyr Ile Glu Tyr Gly Ile Gln Arg Ile
        435                 440                 445

Thr Cys Pro Asn Val Asp Gly Tyr Phe Pro Ser Ser Val Lys Pro Thr
    450                 455                 460

Ile Thr Trp Tyr Met Gly Cys Tyr Lys Ile Gln Asn Phe Asn Asn Val
465                 470                 475                 480

Ile Pro Glu Gly Met Asn Leu Ser Phe Leu Ile Ala Leu Ile Ser Asn
                485                 490                 495

Asn Gly Asn Tyr Thr Cys Val Val Thr Tyr Pro Glu Asn Gly Arg Thr
            500                 505                 510

Phe His Leu Thr Arg Thr Leu Thr Val Lys Val Val Gly Ser Pro Lys
        515                 520                 525

Asn Ala Val Pro Pro Val Ile His Ser Pro Asn Asp His Val Val Tyr
    530                 535                 540

Glu Lys Glu Pro Gly Glu Glu Leu Leu Ile Pro Cys Thr Val Tyr Phe
545                 550                 555                 560
```

```
Ser Phe Leu Met Asp Ser Arg Asn Glu Val Trp Trp Thr Ile Asp Gly
            565                 570                 575

Lys Lys Pro Asp Asp Ile Thr Ile Asp Val Thr Ile Asn Glu Ser Ile
            580                 585                 590

Ser His Ser Arg Thr Glu Asp Glu Thr Arg Thr Gln Ile Leu Ser Ile
        595                 600                 605

Lys Lys Val Thr Ser Glu Asp Leu Lys Arg Ser Tyr Val Cys His Ala
        610                 615                 620

Arg Ser Ala Lys Gly Glu Val Ala Lys Ala Lys Val Lys Gln Lys
625                 630                 635                 640

Val Pro Ala Pro Arg Tyr Thr Val Glu Asp Lys Thr His Thr Cys Pro
                645                 650                 655

Pro Cys Pro Ala Pro Glu Leu Leu Gly Gly Pro Ser Val Phe Leu Phe
                660                 665                 670

Pro Pro Lys Pro Lys Asp Thr Leu Met Ile Ser Arg Thr Pro Glu Val
            675                 680                 685

Thr Cys Val Val Val Asp Val Ser His Glu Asp Pro Glu Val Lys Phe
        690                 695                 700

Asn Trp Tyr Val Asp Gly Val Glu Val His Asn Ala Lys Thr Lys Pro
705                 710                 715                 720

Arg Glu Glu Gln Tyr Asn Ser Thr Tyr Arg Val Val Ser Val Leu Thr
                725                 730                 735

Val Leu His Gln Asp Trp Leu Asn Gly Lys Glu Tyr Lys Cys Lys Val
            740                 745                 750

Ser Asn Lys Ala Leu Pro Ala Pro Ile Glu Lys Thr Ile Ser Lys Ala
        755                 760                 765

Lys Gly Gln Pro Arg Glu Pro Gln Val Tyr Thr Leu Pro Pro Ser Arg
770                 775                 780

Asp Glu Leu Thr Lys Asn Gln Val Ser Leu Thr Cys Leu Val Lys Gly
785                 790                 795                 800

Phe Tyr Pro Ser Asp Ile Ala Val Glu Trp Glu Ser Asn Gly Gln Pro
                805                 810                 815

Glu Asn Asn Tyr Lys Thr Thr Pro Pro Val Leu Asp Ser Asp Gly Ser
            820                 825                 830

Phe Phe Leu Tyr Ser Lys Leu Thr Val Asp Lys Ser Arg Trp Gln Gln
        835                 840                 845

Gly Asn Val Phe Ser Cys Ser Val Met His Glu Ala Leu His Asn His
        850                 855                 860

Tyr Thr Gln Lys Ser Leu Ser Leu Ser Pro Gly Lys
865                 870                 875
```

IL-33 ANTAGONISTS AND USES THEREOF

CROSS-REFERENCE TO RELATED APPLICATIONS

This application is a division of U.S. application Ser. No. 14/210,599, filed Mar. 14, 2014, which claims the benefit under 35 USC § 119(e) of U.S. Provisional Application Nos. 61/787,121 (filed Mar. 15, 2013), 61/819,029 (filed May 3, 2013) and 61/913,417 (filed Dec. 9, 2013), each of which is herein specifically incorporated by reference in its entirety.

SEQUENCE LISTING

This application incorporates by reference the Sequence Listing submitted in Computer Readable Form as file 494126-Sequence.txt, created on Mar. 20, 2017 and containing 49,816 bytes.

FIELD OF THE INVENTION

The present invention relates to antigen-binding molecules which are capable of antagonizing IL-33, and methods of use thereof.

BACKGROUND

Interleukin-33 (IL-33) is a ligand for ST2, a toll-like/interleukin-1 receptor super-family member that associates with an accessory protein, IL-1RAcP (for reviews, see, e.g., Kakkar and Lee, *Nature Reviews—Drug Discovery* 7(10): 827-840 (2008), Schmitz et al., *Immunity* 23:479-490 (2005); Liew et al., *Nature Reviews—Immunology* 10:103-110 (2010); US 2010/0260770; US 2009/0041718). Upon activation of ST2/IL-1RAcP by IL-33, a signaling cascade is triggered through downstream molecules such as MyD88 (myeloid differentiation factor 88) and TRAF6 (TNF receptor associated factor 6), leading to activation of NFκB (nuclear factor-κB), among others. IL-33 signaling has been implicated as a factor in a variety of diseases and disorders. (Liew et al., *Nature Reviews—Immunology* 10:103-110 (2010)).

BRIEF SUMMARY OF THE INVENTION

The present invention provides interleukin-33 (IL-33) antagonists.

In one aspect, the invention provides an IL-33 antagonist comprising a first IL-33 binding domain (D1) and a multimerizing domain (M).

In one embodiment, the IL-33 antagonist comprises a first IL-33 binding domain (D1) attached to a multimerizing domain (M), wherein D1 comprises an IL-33-binding portion of an ST2 protein.

In certain embodiments, the IL-33 antagonist further comprises one or more additional IL-33 binding domains (e.g., D2, D3, D4, etc.).

According to certain embodiments, the IL-33 binding domain (D1, D2, D3, D4, etc.) comprises an IL-33-binding portion of an ST2 protein, an extracellular domain of an IL-1RAcP protein, or other IL-33 binding domain.

In one embodiment, the IL-33 antagonist further comprises a second IL-33 binding domain (D2) attached to D1 and/or M, wherein D2 comprises an extracellular portion of an IL-1RAcP protein. In one embodiment, D1 is attached to the N-terminus of M. In one embodiment, D1 is attached to the C-terminus of M. In one embodiment, D2 is attached to the N-terminus of M. In one embodiment, D2 is attached to the C-terminus of M. In one embodiment, D1 is attached to the N-terminus of D2, and D2 is attached to the N-terminus of M.

The multimerizing domain (M) may be a peptide or polypeptide having a N-terminus and a C-terminus. The IL-33 binding domain components may be attached to either the N-terminus or the C-terminus of M. According to certain embodiments, the D1, D2 and M components are attached in tandem, such that D1 is attached to the N-terminus of D2, and D2 is attached to the N-terminus of M. Numerous arrangements and configurations of the D1, D2, and M components are contemplated within the scope of the present invention, examples of which are described herein.

In one embodiment, the IL-33 antagonist binds human interleukin 33 (IL-33) with a binding dissociation equilibrium constant ($K_D$) of less than about 80 pM as measured in a surface plasmon resonance assay at 25° C., and/or a binding dissociation equilibrium constant ($K_D$) of less than about 400 pM as measured in a surface plasmon resonance assay at 37° C.

In one embodiment, the IL-33 antagonist binds human interleukin 33 (IL-33) with a binding dissociation equilibrium constant ($K_D$) of less than about 60 pM as measured in a surface plasmon resonance assay at 25° C., and/or a binding dissociation equilibrium constant ($K_D$) of less than about 1.0 pM as measured in a surface plasmon resonance assay at 37° C.

In one embodiment, the IL-33 antagonist binds monkey interleukin 33 (IL-33) with a binding dissociation equilibrium constant ($K_D$) of less than about 60 pM as measured in a surface plasmon resonance assay at 25° C., and/or a binding dissociation equilibrium constant ($K_D$) of less than about 200 pM as measured in a surface plasmon resonance assay at 37° C.

In one embodiment, the IL-33 antagonist binds monkey interleukin 33 (IL-33) with a binding dissociation equilibrium constant ($K_D$) of less than about 1.0 pM as measured in a surface plasmon resonance assay at 25° C., and/or a binding dissociation equilibrium constant ($K_D$) of less than about 1.0 pM as measured in a surface plasmon resonance assay at 37° C.

In one embodiment, the IL-33 antagonist binds mouse interleukin 33 (IL-33) with a binding dissociation equilibrium constant ($K_D$) of less than about 110 pM as measured in a surface plasmon resonance assay at 25° C., and/or a binding dissociation equilibrium constant ($K_D$) of less than about 100 pM as measured in a surface plasmon resonance assay at 37° C.

In one embodiment, the IL-33 antagonist binds mouse interleukin 33 (IL-33) with a binding dissociation equilibrium constant ($K_D$) of less than about 10 pM as measured in a surface plasmon resonance assay at 25° C., and/or a binding dissociation equilibrium constant ($K_D$) of less than about 5 pM as measured in a surface plasmon resonance assay at 37° C.

In one embodiment, the IL-33 antagonist binds human interleukin 33 (IL-33) with a dissociative half-life (t½) of greater than or equal to about 9 minutes as measured in a surface plasmon resonance assay at 25° C., and/or a dissociative half-life (t½) of greater than or equal to about 4 minutes as measured in a surface plasmon resonance assay at 37° C.

In one embodiment, the IL-33 antagonist binds human interleukin 33 (IL-33) with a dissociative half-life (t½) of greater than or equal to about 30 minutes as measured in a surface plasmon resonance assay at 25° C., and/or a dissociative half-life (t½) of greater than or equal to about 1000 minutes as measured in a surface plasmon resonance assay at 37° C.

In one embodiment, the IL-33 antagonist binds monkey interleukin 33 (IL-33) with a dissociative half-life (t½) of greater than about 40 minutes as measured in a surface plasmon resonance assay at 25° C., and/or a dissociative half-life (t½) of greater than or equal to about 10 minutes as measured in a surface plasmon resonance assay at 37° C.

In one embodiment, the IL-33 antagonist binds monkey interleukin 33 (IL-33) with a dissociative half-life (t½) of greater than about 1000 minutes as measured in a surface plasmon resonance assay at 25° C., and/or a dissociative half-life (t½) of greater than or equal to about 1000 minutes as measured in a surface plasmon resonance assay at 37° C.

In one embodiment, the IL-33 antagonist binds mouse interleukin 33 (IL-33) with a dissociative half-life (t½) of greater than about 25 minutes as measured in a surface plasmon resonance assay at 25° C., and/or a dissociative half-life (t½) of greater than about 30 minutes as measured in a surface plasmon resonance assay at 37° C.

In one embodiment, the IL-33 antagonist binds mouse interleukin 33 (IL-33) with a dissociative half-life (t½) of greater than about 500 minutes as measured in a surface plasmon resonance assay at 25° C., and/or a dissociative half-life (t½) of greater than about 1000 minutes as measured in a surface plasmon resonance assay at 37° C.

In one embodiment, the IL-33 antagonist blocks the interaction of IL-33 and ST2.

In one embodiment, the IL-33 antagonist blocks the interaction of IL-33 and ST2 with an $IC_{50}$ value of less than about 115 pM as measured in an in vitro receptor/ligand binding assay at 25° C.

In one embodiment, the IL-33 antagonist blocks the interaction of IL-33 and ST2 with an $IC_{50}$ value of less than about 20 pM as measured in an in vitro receptor/ligand binding assay at 25° C.

In one embodiment, D1 comprises the amino acid sequence of SEQ ID NO: 5 or 6, or an amino acid sequence having at least 90% identity thereto.

In one embodiment, D2 comprises the amino acid sequence of SEQ ID NO: 7 or 8, or an amino acid sequence having at least 90% identity thereto.

In one embodiment the multimerizing component comprises the amino acid sequence of SEQ ID NO: 9 or 10, or an amino acid sequence having at least 90% identity thereto.

In one embodiment, the IL-33 antagonist comprises a first IL-33 binding domain (D1) attached to a first multimerizing domain (M1), and a second IL-33 binding domain (D2) attached to a second multimerizing domain (M2), wherein the D1 and/or D2 domains comprise an IL-33-binding portion of a receptor selected from the group consisting of ST2 and IL-1RAcP.

In one embodiment, the IL-33 antagonist comprises a third IL-33 binding domain (D3), which is attached to either D1 or M1, and wherein D3 comprises an IL-33-binding portion of a receptor selected from the group consisting of ST2 and IL-1RAcP.

In one embodiment, the IL-33 antagonist comprises a fourth IL-33 binding domain (D4), which is attached to either D2 or M2, and wherein D4 comprises an IL-33-binding portion of a receptor selected from the group consisting of ST2 and IL-1RAcP.

In one embodiment, D1 is attached to the N-terminus of M1, and D2 is attached to the N-terminus of M2.

In one embodiment, D3 is attached to the N-terminus of D1.

In one embodiment, D3 is attached to the C-terminus of M1.

In one embodiment, D4 is attached to the N-terminus of D2.

In one embodiment, D4 is attached to the C-terminus of M2.

In one embodiment, D3 is attached to the N-terminus of D1, D1 is attached to the N-terminus of M1; D4 is attached to the N-terminus of D2, and D2 is attached to the N-terminus of M2.

In one embodiment, D3 is identical or substantially identical to D4 and D1 is identical or substantially identical to D2.

In one embodiment D3 and D4 each comprise an IL-33-binding portion of an ST2 protein; and D1 and D2 each comprise an extracellular portion of an IL-1RAcP protein.

In one embodiment, the IL-33 antagonist comprises an amino acid sequence selected from the group consisting of SEQ ID NOs: 1, 2, 3, 4 and 13.

A second aspect of the invention provides methods of using the IL-33 antagonists described herein for treating an inflammatory disease or disorder, or at least one symptom associated with the inflammatory disease or disorder, the method comprising administering one or more IL-33 antagonists of the invention, or a pharmaceutical composition containing one or more IL-33 antagonists of the invention, to a patient in need thereof, wherein the inflammatory disease or disorder is alleviated, or reduced in severity, duration or frequency of occurrence, or at least one symptom associated with the inflammatory disease or disorder is alleviated, or reduced in severity, duration, or frequency of occurrence.

In one embodiment, the inflammatory disease or disorder that may be treated with any one or more IL-33 antagonists of the invention may be selected from the group consisting of asthma, atopic dermatitis, chronic obstructive pulmonary disease (COPD), inflammatory bowel disease, multiple sclerosis, arthritis, allergic rhinitis, eosinophilic esophagitis and psoriasis.

In one embodiment, the inflammatory disease or disorder that may be treated with any one or more IL-33 antagonists of the invention is asthma. The asthma may be eosinophilic or non-eosinophilic asthma. The asthma may be steroid resistant or steroid sensitive asthma.

In one embodiment, the inflammatory disease or disorder that may be treated with any one or more IL-33 antagonists of the invention is atopic dermatitis.

In one embodiment, the inflammatory disease or disorder that may be treated with any one or more IL-33 antagonists of the invention is chronic obstructive pulmonary disease (COPD). In one embodiment, the chronic obstructive pulmonary disease may result from, or may be caused in part by cigarette smoke.

In a related embodiment, the invention provides a method for treating a patient who demonstrates a sensitivity to an allergen, the method comprising administering an effective amount of one or more of the IL-33 antagonists of the invention, or a pharmaceutical composition comprising one or more of the IL-33 antagonists of the invention, to a patient in need thereof, wherein the patient demonstrates a reduced sensitivity to, or a diminished allergic reaction against the allergen, or does not experience any sensitivity or allergic reaction to, or anaphylactic response to the allergen following administration of the antibody or a composition comprising the antibody.

In a related embodiment, the invention provides a pharmaceutical composition comprising one or more of the IL-33 antagonists of the invention for use in treating an inflammatory disease or disorder, wherein the inflammatory disease or disorder is selected from the group consisting of asthma, allergy, anaphylaxis, atopic dermatitis, chronic obstructive pulmonary disease (COPD), inflammatory bowel disease, multiple sclerosis, arthritis, allergic rhinitis, eosinophilic esophagitis and psoriasis.

In one embodiment, the invention provides a pharmaceutical composition comprising one or more of the IL-33 antagonists of the invention in the manufacture of a medicament for the treatment of an inflammatory disease or disorder, wherein the inflammatory disease or disorder is selected from the group consisting of asthma, allergy, anaphylaxis, atopic dermatitis, chronic obstructive pulmonary disease (COPD), inflammatory bowel disease, multiple sclerosis, arthritis, allergic rhinitis, eosinophilic esophagitis and psoriasis.

In certain embodiments, the invention provides a method of treating an inflammatory disease or disorder by administering one or more of the IL-33 antagonists of the invention in combination with an effective amount of a second therapeutic agent useful for alleviating the inflammatory disease or disorder, or at least one symptom of the inflammatory disease or disorder, or for diminishing an allergic response to an allergen.

In one embodiment, the second therapeutic agent may be selected from the group consisting of a non-steroidal anti-inflammatory (NSAID), a corticosteroid, a bronchial dilator, an antihistamine, epinephrine, a decongestant, a thymic stromal lymphopoietin (TSLP) antagonist, an IL-13 antagonist, an IL-4 antagonist, an IL-4/IL-13 dual antagonist, an IL-5 antagonist, an IL-6 antagonist, an IL-12/23 antagonist, an IL-22 antagonist, an IL-25 antagonist, an IL-17 antagonist, an IL-31 antagonist, a PDE4 inhibitor and another IL-33 antagonist or a different antibody to IL-33.

A third aspect of the invention provides a pharmaceutical composition comprising any one or more of the IL-33 antagonists described herein and a pharmaceutically acceptable carrier or diluent and therapeutic methods comprising administering such pharmaceutical compositions to subjects in need thereof. In certain embodiments, an additional therapeutically active component is formulated with, or administered in combination with an IL-33 antagonist of the present invention.

Other embodiments will become apparent from a review of the ensuing detailed description.

BRIEF DESCRIPTION OF THE FIGURE

FIG. 1 shows four exemplary arrangements of the individual components of the IL-33 antagonists relative to one another. Panel A shows an arrangement in which a first IL-33-binding domain (D1) is attached to the N-terminus of a first multimerizing domain (M1), and a second IL-33-binding domain (D2) is attached to the N-terminus of a second multimerizing domain (M2). D1 is shown as a white box and D2 is shown as a black box to indicate that D1 and D2 are derived from different IL-33 binding proteins. Panel B shows an arrangement in which a first IL-33-binding domain (D1) is attached to the N-terminus of a first multimerizing domain (M1), and a second IL-33-binding domain (D2) is attached to the C-terminus of a second multimerizing domain (M2). D1 is shown as a white box and D2 is shown as a black box to indicate that D1 and D2 are derived from different IL-33 binding proteins. Panels C and D show arrangements comprising four IL-33-binding domains, D1, D2, D3 and D4. In these arrangements, D3-D1-M1 and D4-D2-M2 are attached in tandem, wherein D3 is attached to the N-terminus of D1, and D1 is attached to the N-terminus of M1; and D4 is attached to the N-terminus of D2, and D2 is attached to the N-terminus of M2. In Panel C, D3 and D4 are identical or substantially identical to one another, and D1 and D2 are identical or substantially identical to one another. In Panel D, D1 and D4 are identical or substantially identical to one another, and D3 and D2 are identical or substantially identical to one another.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

IL-33 Antagonists

The expressions "interleukin-33," "IL-33," and the like, as used herein, refer to a human IL-33 protein having the amino acid sequence as set forth in NCBI accession Nos. NP_254274.1 (human isoform 1), NP_001186569.1 (human isoform 2), or NP_001186570.1 (human isoform 3). All references to proteins, polypeptides and protein fragments herein are intended to refer to the human version of the respective protein, polypeptide or protein fragment unless explicitly specified as being from a non-human species (e.g., "mouse IL-33," "monkey IL-33," etc.).

As used herein, the expression "IL-33 antagonist" means any antigen-binding molecule that is capable of binding IL-33 and blocking, attenuating or otherwise interfering with IL-33 signaling and/or the interaction between IL-33 and a cell surface receptor (e.g., ST2).

The IL-33 antagonists of the present invention comprise a first IL-33 binding domain (D1) attached to a multimerizing domain (M). In certain embodiments, the IL-33 antagonists of the invention comprise a second IL-33 binding domain (D2) attached to D1 and/or M. According to certain embodiments, D1 comprises an IL-33-binding portion of an ST2 protein. According to certain embodiments, D2 comprises an extracellular portion of an IL-1RAcP protein.

The individual components of the IL-33 antagonists may be arranged relative to one another in a variety of ways that result in functional antagonist molecules capable of binding IL-33. For example, D1 and/or D2 may be attached to the N-terminus of M. In other embodiments D1 and/or D2 is attached to the C-terminus of M. In yet other embodiments, D1 is attached to the N-terminus of D2, and D2 is attached to the N-terminus of M, resulting in an in-line fusion, from N- to C-terminus, of an antagonist molecule represented by the formula D1-D2-M. Other orientations of the individual components are disclosed elsewhere herein.

Non-limiting examples of IL-33 antagonists of the invention are shown in the working embodiments herein, and include the antagonists designated "hST2-hFc," "hST2-mFc," "hST2-hIL1RAcP-mFc," "hST2-hIL1RAcP-hFc" and "mST2-mIL1RAcP-mFc". hST2-hFc and hST2-mFc may also be referred to as "ST2 receptor proteins". hST2-hIL1RAcP-mFc, hST2-hIL1RAcP-hFc and mST2-mIL1RAcP-mFc may also be referred to herein as "IL-33 Trap proteins".

As used herein, the term "attached", in the context of a first polypeptide component being "attached" to a second polypeptide component (e.g., "D1 is attached to M," "D2 is attached to M," "D1 is attached to D2," etc.), means that the first component is physically connected to the second component either directly or indirectly. As an example of a direct attachment between two polypeptide components, the C-terminal amino acid of the first component may be connected via a peptide bond to the N-terminal amino acid of the second component, or the N-terminal amino acid of the first component may be connected via a peptide bond to the C-terminal amino acid of the second component. Indirect attachment, on the other hand, means that the first and second components are each connected physically to different parts of an intervening structure which serves as a link between the first and second components. The intervening structure may be, e.g., a single amino acid, a peptide linker, or another polypeptide component (e.g., another IL-33-binding protein, etc.). For example, in the arrangement D1-D2-M (wherein a first IL-33 binding domain [D1] is attached to a second IL-33 binding domain [D2] which in turn is connected to a multimerizing domain [M]), D1 is regarded as being "attached" to M, even though the attachment is indirect with D2 serving as an intervening structure.

Standard molecular biological techniques (e.g., recombinant DNA technology) may be used to construct any of the IL-33 antagonists of the invention or variants thereof.

IL-33-Binding Domains

The IL-33 antagonists of the present invention comprise at least one IL-33 binding domain (sometimes referred to herein by the designation "D," or "D1," "D2," etc.). In certain embodiments, the IL-33 binding domain comprises an IL-33-binding portion of an ST2 protein. An IL-33-binding portion of an ST2 protein can comprise or consist of all or part of the extracellular domain of an ST2 protein. In certain embodiments, an ST2 protein is a human ST2 protein. A "human ST2 protein," as used herein, refers to an ST2 protein having the amino acid sequence of SEQ ID NO:12. In certain embodiments, the ST2 protein is an ST2 protein from a non-human species (e.g., mouse ST2, monkey ST2, etc). An exemplary IL-33-binding portion of an ST2 protein is set forth herein as the amino acid sequence of SEQ ID NO:5 (corresponding to the extracellular domain of human ST2 [K19-5328 of NCBI Accession No. NP_057316.3]). Another example of an IL-33-binding portion of an ST2 protein is set forth herein as the amino acid sequence of SEQ ID NO:6 (corresponding to the extracellular domain of mouse ST2 [S27-R332 of NCBI Accession No. P14719]).

In certain embodiments, the IL-33 binding domain comprises an extracellular portion of an IL-1RAcP protein. In certain embodiments, an IL-1RAcP protein is a human IL-1RAcP protein. A "human IL-1RAcP protein," as used herein, refers to an IL-1RAcP protein having the amino acid sequence of SEQ ID NO:13. In certain embodiments, the IL-1RAcP protein is an IL-1RAcP protein from a non-human species (e.g., mouse IL-1RAcP, monkey IL-1RAcP, etc). An exemplary extracellular portion of an IL-1RAcP protein is set forth herein as the amino acid sequence of SEQ ID NO:7 (corresponding to the extracellular domain of human IL-1RAcP [S21-E359 of NCBI Accession No. Q9NPH3]). Another example of an extracellular portion of an IL-1RAcP protein is set forth herein as the amino acid sequence of SEQ ID NO:8 (corresponding to the extracellular domain of mouse IL-1RAcP [S21-E359 of NCBI Accession No. Q61730]).

The present invention includes IL-33 antagonists comprising D1 and/or D2 components having an amino acid sequence that is at least 80%, 85%, 90%, 91%, 92%, 93%, 94%, 95%, 96%, 97%, 98% or 99% identical to any of the exemplary IL-33 binding domain component amino acid sequences set forth herein (e.g., SEQ ID NOs:5-8).

Multimerizing Domain

The IL-33 antagonists of the present invention also comprise at least one multimerizing domain (sometimes referred to herein by the abbreviation "M," "M1", "M2", etc.). In general terms, the multimerizing domain(s) of the present invention function to connect the various components of the IL-33 antagonists (e.g., the IL-33-binding domain(s)) with one another. As used herein, a "multimerizing domain" is any macromolecule that has the ability to associate (covalently or non-covalently) with a second macromolecule of the same or similar structure or constitution. For example, a multimerizing domain may be a polypeptide comprising an immunoglobulin $C_H3$ domain. A non-limiting example of a multimerizing domain is an Fc portion of an immunoglobulin, e.g., an Fc domain of an IgG selected from the isotypes IgG1, IgG2, IgG3, and IgG4, as well as any allotype within each isotype group. In certain embodiments, the multimerizing domain is an Fc fragment or an amino acid sequence of 1 to about 200 amino acids in length containing at least one cysteine residues. In other embodiments, the multimerizing domain is a cysteine residue or a short cysteine-containing peptide. Other multimerizing domains include peptides or polypeptides comprising or consisting of a leucine zipper, a helix-loop motif, or a coiled-coil motif.

Non-limiting exemplary multimerizing domains that can be used in the IL-33 antagonists of the present invention include human IgG1 Fc (SEQ ID NO:9) or mouse IgG2a Fc (SEQ ID NO:10). The present invention includes IL-33 antagonists comprising M components having an amino acid sequence that is at least 80%, 85%, 90%, 91%, 92%, 93%, 94%, 95%, 96%, 97%, 98% or 99% identical to any of the exemplary M component amino acid sequences set forth herein (e.g., SEQ ID NOs:9 or 10).

In certain embodiments, the IL-33 antagonists of the present invention comprise two multimerizing domains, M1 and M2, wherein M1 and M2 are identical to one another. For example, M1 can be an Fc domain having a particular amino acid sequence, and M2 is an Fc domain with the same amino acid sequence as M1.

Alternatively, in certain embodiments, the IL-33 antagonists of the invention comprise two multimerizing domains, M1 and M2, that differ from one another at one or more amino acid position. For example, M1 may comprise a first immunoglobulin (Ig) $C_H3$ domain and M2 may comprise a second Ig $C_H3$ domain, wherein the first and second Ig $C_H3$ domains differ from one another by at least one amino acid, and wherein at least one amino acid difference reduces binding of the targeting construct to Protein A as compared to a reference construct having identical M1 and M2 sequences. In one embodiment, the Ig $C_H3$ domain of M1 binds Protein A and the Ig $C_H3$ domain of M2 contains a mutation that reduces or abolishes Protein A binding such as an H95R modification (by IMGT exon numbering; H435R by EU numbering). The $C_H3$ of M2 may further comprise a Y96F modification (by IMGT; Y436F by EU). Further modifications that may be found within the $C_H3$ of M2 include: D16E, L18M, N44S, K52N, V57M, and V82I (by IMGT; D356E, L358M, N384S, K392N, V397M, and V422I by EU) in the case of an IgG1 Fc domain; N44S, K52N, and V82I (IMGT; N384S, K392N, and V422I by EU) in the case of an IgG2 Fc domain; and Q15R, N44S, K52N, V57M, R69K, E79Q, and V82I (by IMGT; Q355R, N384S, K392N, V397M, R409K, E419Q, and V422I by EU) in the case of an IgG4 Fc domain.

Orientation and Arrangement of the Components of the IL-33 Antagonists

The individual components of the IL-33 antagonists of the present invention (e.g., D1, D2, M, etc.) can be arranged relative to one another in a variety of ways, examples of which are described in detail elsewhere herein. The multimerizing domains (M1 and/or M2) may be a peptide or polypeptide having a N-terminus and a C-terminus. Thus, D1 and D2 components may be attached to the M component at either the N- or C-terminus of the M component. for example, D1 may be attached to the N-terminus of M (represented as "D1-M"). Alternatively, D1 may be attached to the C-terminus of M (represented as "M-D1"). In some embodiments, D2 is attached to the N-terminus of M (represented as "D2-M"), or D2 is attached to the C-terminus of M (represented as "M-D2"). In yet other embodiments, D1 is attached to the N-terminus of D2, and D2 is attached to the N-terminus of M (represented as "D1-D2-M"). Other exemplary arrangements of the individual components, from N- to C-terminus, may thus be represented as follows: D2-D1-M; M-D1; M-D2; M-D1-D2; M-D2-D1; D1-M-D2; D2-M-D1; etc.

In embodiments comprising two different multimerizing domains (M1 and M2), one or more IL-33 binding domains may be attached to the multimerizing domains in a variety of arrangements. Non-limiting examples of such arrangements are illustrated schematically in FIG. 1. For example, the present invention includes IL-33 antagonists comprising a first IL-33 binding domain (D1) attached to a first multimerizing domain (M1), and a second IL-33 binding domain (D2) attached to a second multimerizing domain (M2). The IL-33 antagonists of the invention may also include one or more additional IL-33 binding domains (e.g., D3, D4, etc.). For example, where a third IL-33 binding domain (D3) is included, the D3 component may be attached to either D1 or M1; likewise, where a fourth IL-33 binding domain (D4) is included, the D4 component may be attached to either D2 or M2.

In embodiments involving multiple IL-33 binding domains, two or more of the IL-33 binding domains may be identical, or substantially identical, to one another. For example, in an embodiment comprising four IL-33 binding domains (D1, D2, D3, and D4), D1 and D2 may be identical, or substantially identical, to one another; and D3 and D4 may be identical, or substantially identical, to one another, etc.

Non-limiting illustrative examples of IL-33 antagonists of the invention comprising two multimerizing domains (M1 and M2) and four IL-33 binding domains (D1, D2, D3 and D4) are shown in FIG. 1, arrangements C and D). In exemplary arrangements of this sort, D1 is attached to the N-terminus of M1, D2 is attached to the N-terminus of M2, D3 is attached to the N-terminus of D1, and D4 is attached to the N-terminus of D2. Panel C depicts the situation wherein D1 and D2 are identical to one another (e.g., each comprising the extracellular domain of IL-1RAcP), and D3 and D4 are identical to one another (e.g., each comprising the extracellular domain of ST2). Panel C depicts the situation wherein D1 and D2 are non-identical, and D3 and D4 are non-identical. Numerous other arrangements will be apparent to a person of ordinary skill in the art based on the teachings of the present disclosure and are encompassed within the scope of the present invention.

Linkers

The individual components of the IL-33 antagonists of the present invention (e.g., D1, D2, M1, M2, etc.) may be attached to one another directly (e.g., D1 and/or D2 may be directly attached to M, etc.); alternatively, the individual components may be attached to one another via a linker component (e.g., D1 and/or D2 may be attached to M via a linker oriented between the individual components; D1 may be attached to D2 via a linker; etc.). In any of the arrangements disclosed herein, wherein one component is described as being "attached" to another component, the attachment may be through a linker (even if not specifically designated as such). As used herein, a "linker" is any molecule that joins two polypeptide components together. For example, a linker may be a peptide comprising from 1 to 20 amino acids connected together via peptide bonds. (A peptide bond per se, however, is not considered a "linker" for purposes of the present disclosure). In certain embodiments, the linker comprises sterically unhindered amino acids such as glycine and alanine. In certain embodiments, the linker is a flexible chain of amino acids that is resistant to proteolytic degradation. A linker may comprise two molecular structures that interact with one another. For example, in certain embodiments a linker may comprise a streptavidin component and a biotin component; the association between streptavidin (attached to one component) and biotin (attached to another component) serves as an attachment between individual components of the IL-33 antagonists. The exemplary IL-33 antagonists described herein as hST2-hIL1RAcP-mFc and mST2-mIL1RAcP-mFc include a serine-glycine (SG) linker between the IL-1RAcP component and the Fc multimerizing domain. Other similar linker arrangements and configurations involving linkers are contemplated within the scope of the present invention.

Biological Characteristics of the IL-33 Antagonists

The present invention includes IL-33 antagonists that bind soluble IL-33 molecules with high affinity. For example, the present invention includes IL-33 antagonists (as described elsewhere herein) that bind IL-33 (e.g., at 25° C. or 37° C.) with a $K_D$ of less than about 400 pM as measured by surface plasmon resonance, e.g., using the assay format as defined in Example 2 herein. In certain embodiments, the IL-33 antagonists of the present invention bind IL-33 with a $K_D$ of less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 9 pM, less than about 8 pM, less than about 6 pM, or less than about 1 pM as measured by surface plasmon resonance, e.g., using the assay format as defined in Example 2 herein, or a substantially similar assay.

The present invention also includes IL-33 antagonists that specifically bind IL-33 with a dissociative half-life (t½) of greater than or equal to about 4 minutes as measured by surface plasmon resonance at 25° C. or 37° C., e.g., using the assay format as defined in Example 2 herein, or a substantially similar assay. In certain embodiments, the IL-33 antagonists of the present invention bind IL-33 with a t½ of greater than about 10 minutes, greater than about 20 minutes, greater than about 30 minutes, greater than about 40 minutes, greater than about 50 minutes, greater than about 60 minutes, or greater than about 70 minutes, or greater than about 500 minutes, or greater than about 1000 minutes as measured by surface plasmon resonance at 25° C. or 37° C., e.g., using the assay format as defined in Example 2 herein, or a substantially similar assay.

The present invention also includes IL-33 antagonists that block the binding of IL-33 to an IL-33 receptor (e.g., ST2). For example, the present invention includes IL-33 antagonists that block the binding of IL-33 to ST2 in vitro, with an $IC_{50}$ value of less than about 115 pM, as measured by an ELISA-based immunoassay, e.g., using the assay format as defined in Example 3 herein, or a substantially similar assay. In certain embodiments, the IL-33 antagonists of the present invention block the binding of IL-33 to ST2 in vitro with an $IC_{50}$ value of less than about 120 pM, less than about 90 pM, less than about 80 pM, less than about 70 pM, less than about 60 pM, less than about 50 pM, less than about 40 pM, less than about 30 pM, less than about 20 pM, less than about 18 pM, less than about 16 pM, less than about 14 pM, less than about 12 pM, less than about 10 pM, less than about 9 pM, less than about 8 pM, or less than about 7 pM, as measured by an ELISA-based immunoassay, e.g., using the assay format as defined in Example 3 herein, or a substantially similar assay.

The present invention also includes IL-33 antagonists that inhibit IL-33-mediated cell signaling. For example, the present invention includes IL-33 antagonists that inhibit IL-33-mediated signaling in cells expressing human ST2, with an $IC_{50}$ value of less than about 500 pM, as measured in a cell-based blocking bioassay, e.g., using the assay format as defined in Example 4 herein, or a substantially similar assay. In certain embodiments, the IL-33 antagonists of the present invention block IL-33-mediated signaling in cells expressing human ST2, with an $IC_{50}$ of less than about 400 pM, less than about 300 pM, less than about 200 pM, less than about 100 pM, less than about 80 pM, less than about 60 pM, less than about 40 pM, less than about 30 pM, less than about 20 pM, less than about 18 pM, less than about 16 pM, less than about 14 pM, less than about 12 pM, less than about 10 pM, less than about 8 pM, less than about 7 pM, less than about 6 pM, less than about 5 pM, less than about 4 pM, less than about 3 pM, less than about 2 pM, or less than about 1.5 pM, as measured in a cell-based blocking bioassay, e.g., using the assay format as defined in Example 4 herein, or a substantially similar assay.

The present invention also includes IL-33 antagonists that inhibit IL-33-induced basophil activation and IL-33 antagonists that inhibit IL-33-induced IFN-gamma release from human PBMCs. Basophil activation can be defined as degranulation, cell surface marker expression, cytokine release, and other immune mediator release, such as histamines and leukotrienes.

The IL-33 antagonists of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Therapeutic Formulation and Administration

The invention provides pharmaceutical compositions comprising the IL-33 antagonists of the present invention. The pharmaceutical compositions of the invention may be formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of IL-33 antagonist administered to a patient may vary depending upon the age and the size of the patient, target disease, conditions, route of administration, and the like. The preferred dose is typically calculated according to body weight or body surface area. When an IL-33 antagonist of the present invention is used for treating a condition or disease associated with IL-33 activity in an adult patient, it may be advantageous to intravenously administer the antagonist of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering IL-33 antagonist may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park, Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antagonist or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antagonist molecule contained is generally about 5 to about 500 mg per dosage form in a unit dose; especially in the form of injection, it is preferred that the aforesaid antagonist molecule is contained in about 5 to about 100 mg and in about 10 to about 250 mg for the other dosage forms.

Therapeutic Uses of the IL-33 Antagonists

Experiments conducted by the present inventors have contributed to the identification of various diseases and conditions that can be treated, prevented and/or ameliorated by IL-33 antagonism. For example, hydrodynamic delivery of mouse IL-33 DNA resulted in the induction of lung mucus accumulation and increases in total serum IgE in mice. In addition, mIL-33 DNA delivery resulted in up-regulation of ST2 and various downstream cytokines as measured by microarray analysis. Experiments conducted by the present inventors using IL-33 knock-out mice also revealed various potential therapeutic benefits of IL-33 antagonism. For example, macroscopic scoring and skin infiltrates were found to be comparable between wild-type mice and IL-33$^{-/-}$ mice in a model of IMQ-induced psoriasis. Moreover, IL-33$^{-/-}$ mice showed reduced eosinophilia and residual mucus accumulation in an allergen-induced lung inflammation model. The IL-33 antagonists of the invention are useful, inter alia, for the treatment, prevention and/or amelioration of any disease or disorder associated with or mediated by IL-33 expression, signaling, or activity, or treatable by blocking the interaction between IL-33 and a IL-33 ligand (e.g., ST2) or otherwise inhibiting IL-33 activity and/or signaling. For example, the present invention provides methods for treating infectious diseases (e.g., *Leishmania* infection, *Trichuris* infection, *Mycobacterium* infection, *Listeria* infection, *Toxoplasma* infection, *Schistosoma* infection, respiratory syncytial virus infection, influenza virus infection, etc.), asthma (e.g., eosinophilic or non-eosinophilic asthma, steroid resistant or steroid sensitive asthma, allergic asthma, non-allergic asthma, severe refractory asthma, asthma exacerbations [e.g., viral- or allergen-induced], etc.), atopic dermatitis, psoriasis, other inflammatory disorders, allergy, anaphylaxis, cardiovascular disease, central nervous system disease, pain, and arthritis (e.g., rheumatoid arthritis, osteoarthritis, psoriatic arthritis, etc.), giant cell arteritis, inflammatory bowel disease (e.g Crohn's disease or ulcerative colitis), multiple sclerosis, allergic rhinitis, eosinophilic esophagitis vasculitis, and Henoch-schonlein purpura. The IL-33 antagonists of the present invention are also useful for the treatment, prevention and/or amelioration of one or more fibrotic diseases. Exemplary fibrotic diseases that are treatable by administering the IL-33 antagonists of the invention include pulmonary fibrosis (e.g., idiopathic pulmonary fibrosis, bleomycin-induced pulmonary fibrosis, asbestos-induced pulmonary fibrosis, and bronchiolitis obliterans syndrome), chronic asthma, fibrosis associated with acute lung injury and acute respiratory distress (e.g., allergen induced fibrosis, bacterial pneumonia induced fibrosis, trauma induced fibrosis, viral pneumonia induced fibrosis, ventilator induced fibrosis, non-pulmonary sepsis induced fibrosis and aspiration induced fibrosis), silicosis, radiation-induced fibrosis, chronic obstructive pulmonary disease (COPD, including COPD exacerbations, or COPD resulting from, or caused in part by first or second hand cigarette smoke. ocular fibrosis, skin fibrosis (e.g., scleroderma), hepatic fibrosis (e.g., cirrhosis, alcohol-induced liver fibrosis, non-alcoholic steatohepatitis (NASH), bilary duct injury, primary bilary cirrhosis, infection- or viral-induced liver fibrosis [e.g., chronic HCV infection], autoimmune hepatitis), kidney (renal) fibrosis, cardiac fibrosis, atherosclerosis, stent restenosis, and myelofibrosis.

In the context of the methods of treatment described herein, the IL-33 antagonists may be administered as a monotherapy (i.e., as the only therapeutic agent) or in combination with one or more additional therapeutic agents (examples of which are described elsewhere herein).

Combination Therapies and Formulations

The present invention includes compositions and therapeutic formulations comprising any of the IL-33 antagonists described herein in combination with one or more additional therapeutically active components, and methods of treatment comprising administering such combinations to subjects in need thereof. The IL-33 antagonists of the present invention may also be co-formulated with and/or administered in combination with, e.g., cytokine inhibitors or antagonists, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, IL-21, IL-22, IL-23, IL-25, IL-26, IL-31, an IL-4/IL-13 dual antagonist, an IL-12/IL-23 antagonist, a PDE4 inhibitor (in one embodiment, an oral PDE4 inhibitor), and another IL-33 antagonist or a different antibody to IL-33, thymic stromal lymphopoietin (TSLP), or antagonists of their respective receptors.

The IL-33 antagonists of the invention may also be administered and/or co-formulated in combination with antivirals, antibiotics, analgesics, corticosteroids, steroids, oxygen, antioxidants, metal chelators, IFN-gamma, and/or NSAIDs, a bronchial dilator, an antihistamine, epinephrine, or a decongestant.

The additional therapeutically active component(s) may be administered just prior to, concurrent with, or shortly after the administration of an IL-33 antagonist of the present invention; (for purposes of the present disclosure, such administration regimens are considered the administration of an IL-33 antagonist "in combination with" an additional therapeutically active component). The present invention includes pharmaceutical compositions in which an IL-33 antagonist of the present invention is co-formulated with one or more of the additional therapeutically active component(s) as described elsewhere herein.

Administration Regimens

According to certain embodiments of the present invention, multiple doses of an IL-33 antagonist (or a pharmaceutical composition comprising a combination of an IL-33 antagonist and any of the additional therapeutically active agents mentioned herein) may be administered to a subject over a defined time course. The methods according to this aspect of the invention comprise sequentially administering to a subject multiple doses of an IL-33 antagonist of the invention. As used herein, "sequentially administering" means that each dose of IL-33 antagonist is administered to the subject at a different point in time, e.g., on different days separated by a predetermined interval (e.g., hours, days, weeks or months). The present invention includes methods which comprise sequentially administering to the patient a single initial dose of an IL-33 antagonist, followed by one or more secondary doses of the IL-33 antagonist, and optionally followed by one or more tertiary doses of the IL-33 antagonist.

The terms "initial dose," "secondary doses," and "tertiary doses," refer to the temporal sequence of administration of the IL-33 antagonist of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of IL-33 antagonist, but generally may differ from one another in terms of frequency of administration. In certain embodiments, however, the amount of IL-33 antagonist contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of IL-33 antagonist which is administered to a patient prior to the administration of the very next dose in the sequence with no intervening doses.

The methods according to this aspect of the invention may comprise administering to a patient any number of secondary and/or tertiary doses of an IL-33 antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Construction of IL-33 Antagonists

Five different exemplary IL-33 antagonists of the invention were constructed using standard molecular biological techniques. The first IL-33 antagonist (hST2-hFc, SEQ ID NO:1) consists of the soluble extracellular region of human ST2 (SEQ ID NO:5) fused at its C-terminus to the N-terminus of a human IgG1 Fc region (SEQ ID NO:9). The second IL-33 antagonist (hST2-mFc, SEQ ID NO:2) consists of the soluble extracellular region of human ST2 (SEQ ID NO:5) fused at its C-terminus to the N-terminus of a mouse IgG2a Fc region (SEQ ID NO:10). The third IL-33 antagonist (hST2-hIL1RAcP-mFc, SEQ ID NO: 3) consists of an in-line fusion having human ST2 (SEQ ID NO:5) at its N-terminus, followed by the extracellular region of human IL-1RAcP (SEQ ID NO:7), followed by a mouse IgG2a Fc (SEQ ID NO:10) at its C-terminus. The fourth IL-33 antagonist (mST2-mIL1RAcP-mFc, SEQ ID NO: 4) consists of an in-line fusion having mouse ST2 (SEQ ID NO:6) at its N-terminus, followed by the extracellular region of mouse IL-1RAcP (SEQ ID NO:8), followed by a mouse IgG2a Fc (SEQ ID NO:10) at its C-terminus. The fifth IL-33 antagonist (hST2-hIL1RAcP-hFc, SEQ ID NO:13) consists of an in line fusion having human ST2 of SEQ ID NO: 5 at its N-terminus, followed by the extracellular region of human IL-1RAcP (SEQ ID NO: 7) followed by a human IgG1 Fc (SEQ ID NO: 9) at its C terminus. Table 1a sets forth a summary description of the different IL-33 antagonists and their component parts. Table 1b sets forth the amino acid sequences of the IL-33 antagonists and their component parts.

TABLE 1a

Summary of IL-33 Antagonists

| IL-33 Antagonist | Amino Acid Sequence of Full Antagonist Molecule | D1 Component | D2 Component | M Component |
| --- | --- | --- | --- | --- |
| hST2-hFc | SEQ ID NO: 1 | human ST2 extracellular (SEQ ID NO: 5) | Absent | human IgG1 Fc (SEQ ID NO: 9) |
| hST2-mFc | SEQ ID NO: 2 | human ST2 extracellular (SEQ ID NO: 5) | Absent | mouse IgG2a Fc (SEQ ID NO: 10) |
| hST2-hIL1RAcP-mFc | SEQ ID NO: 3 | human ST2 extracellular (SEQ ID NO: 5) | human IL-1RAcP extracellular (SEQ ID NO: 7) | mouse IgG2a Fc (SEQ ID NO: 10) |
| mST2-mIL1RAcP-mFc | SEQ ID NO: 4 | mouse ST2 extracellular (SEQ ID NO: 6) | mouse IL-1RAcP extracellular (SEQ ID NO: 8) | mouse IgG2a Fc (SEQ ID NO: 10) |
| hST2-hIL1RAcP-hFc | SEQ ID NO: 13 | human ST2 extracellular (SEQ ID NO: 5) | human IL-1RAcP extracellular (SEQ ID NO: 7) | human IgG1 Fc (SEQ ID NO: 9) |

TABLE 1b

Amino Acid Sequences

| Identifier | Sequence |
| --- | --- |
| SEQ ID NO: 1 (hST2-hFc) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLFPVIGAPAQNEIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHSDKTHTCPPCPAPELL GGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPGK |
| SEQ ID NO: 2 (hST2-mFc) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLFPVIGAPAQNIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHSEPRGPTIKPCPPCKCP APNLLGGPSVFIFPPKIKDVLMISLSPIVTCVVVDVSEDDPDVQISWFVNNVEHT AQTQTHREDYNSTLRVVSALPIQHQDWMSGKEFKCKVNNKDLPAPIERTISKPK GSVRAPQVYVLPPPEEEMTKKQVTLTCMVTDFMPEDIYVEWTNNGKTELNYKN TEPVLDSDGSYFMYSKLRVEKKNWVERNSYSCSVVHEGLHNHHTTKSFSRTPG K |

TABLE Ib-continued

Amino Acid Sequences

| Identifier | Sequence |
| --- | --- |
| SEQ ID NO: 3 (hST2-hIL1RAcP-mFc) | KFSKQSWGLENEALIVRCPRQGKPSYTVDWYYSQTNKSIPTQERNRVFASGQL<br>LKFLPAAVADSGIYTCIVRSPTFNRTGYANVTIYKKQSDCNVPDYLMYSTVSGSE<br>KNSKIYCPTIDLYNWTAPLEWFKNCQALQGSRYRAHKSFLVIDNVMTEDAGDYT<br>CKFIHNENGANYSVTATRSFTVKDEQGFSLFPVIGAPAQNEIKEVEIGKNANLTC<br>SACFGKGTQFLAAVLWQLNGTKITDFGEPRIQQEEGQNQSFSNGLACLDMVLRI<br>ADVKEEDLLLQYDCLALNLHGLRRHTVRLSRKNPIDHHSSERCDDWGLDTMRQI<br>QVFEDEPARIKCPLFEHFLKFNYSTAHSAGLTLIWYWTRQDRDLEEPINFRLPEN<br>RISKEKDVLWFRPTLLNDTGNYTCMLRNTTYCSKVAFPLEVVQKDSCFNSPMKL<br>PVHKLYIEYGIQRITCPNVDGYFPSSVKPTITWYMGCYKIQNFNNVIPEGMNLSFL<br>IALISNNGNYTCVVTYPENGRTFHLTRTLTVKVVGSPKNAVPPVIHSPNDHVVYE<br>KEPGEELLIPCTVYFSFLMDSRNEVWWTIDGKKPDDITIDVTINESISHSRTEDET<br>RTQILSIKKVTSEDLKRSYVCHARSAKGEVAKAAKVKQKVPAPRYTVESGEPRG<br>PTIKPCPPCKCPAPNLLGGPSVFIFPPKIKDVLMISLSPIVTCVVVDVSEDDPDVQI<br>SWFVNNVEVHTAQTQTHREDYNSTLRVVSALPIQHQDWMSGKEFKCKVNNKD<br>LPAPIERTISKPKGSVRAPQVYVLPPPEEEMTKKQVTLTCMVTDFMPEDIYVEVVT<br>NNGKTELNYKNTEPVLDSDGSYFMYSKLRVEKKNWVERNSYSCSVVHEGLHN<br>HHTTKSFSRTPGK |
| SEQ ID NO: 4 (mST2-mIL1RAcP-mFc) | SKSSWGLENEALIVRCPQRGRSTYPVEWYYSDTNESIPTQKRNRIFVSRDRLKF<br>LPARVEDSGIYACVIRSPNLNKTGYLNVTIHKKPPSCNIPDYLMYSTVRGSDKNF<br>KITCPTIDLYNWTAPVQWFKNCKALQEPRFRAHRSYLFIDNVTHDDEGDYTCQF<br>THAENGTNYIVTATRSFTVEEKGFSMFPVITNPPYNHTMEVEIGKPASIACSACF<br>GKGSHFLADVLWQINKTVVGNFGEARIQEEEGRNESSSNDMDCLTSVLRITGVT<br>EKDLSLEYDCLALNLHGMIRHTIRLRRKQPIDHRSERCDDWGLDTMRQIQVFED<br>EPARIKCPLFEHFLKYNYSTAHSSGLTLIWYWTRQDRDLEEPINFRLPENRISKEK<br>DVLWFRPTLLNDTGNYTCMLRNTTYCSKVAFPLEVVQKDSCFNSAMRFPVHKM<br>YIEHGIHKITCPNVDGYFPSSVKPSVTWYKGCTEIVDFHNVLPEGMNLSFFIPLVS<br>NNGNYTCVVTYPENGRLFHLTRTVTVKVVGSPKDALPPQIYSPNDRVVYEKEPG<br>EELVIPCKVYFSFIMDSHNEVWWTIDGKKPDDVTVDITINESVSYSSTEDETRTQI<br>LSIKKVTPEDLRRNYVCHARNTKGEAEQAAKVKQKVIPPRYTVESGEPRGPTIKP<br>CPPCKCPAPNLLGGPSVFIFPPKIKDVLMISLSPIVTCVVVDVSEDDPDVQISWFV<br>NNVEVHTAQTQTHREDYNSTLRVVSALPIQHQDWMSGKEFKCKVNNKDLPAPI<br>ERTISKPKGSVRAPQVYVLPPPEEEMTKKQVTLTCMVTDFMPEDIYVEVVTNNGK<br>TELNYKNTEPVLDSDGSYFMYSKLRVEKKNWVERNSYSCSVVHEGLHNHHTTK<br>SFSRTPGK |
| SEQ ID NO: 5 (human ST2 extracellular domain) | KFSKQSWGLENEALIVRCPRQGKPSYTVDWYYSQTNKSIPTQERNRVFASGQL<br>LKFLPAAVADSGIYTCIVRSPTFNRTGYANVTIYKKQSDCNVPDYLMYSTVSGSE<br>KNSKIYCPTIDLYNWTAPLEWFKNCQALQGSRYRAHKSFLVIDNVMTEDAGDYT<br>CKFIHNENGANYSVTATRSFTVKDEQGFSLFPVIGAPAQNEIKEVEIGKNANLTC<br>SACFGKGTQFLAAVLWQLNGTKITDFGEPRIQQEEGQNQSFSNGLACLDMVLRI<br>ADVKEEDLLLQYDCLALNLHGLRRHTVRLSRKNPIDHHS |
| SEQ ID NO: 6 (mouse sT2 extracellular domain) | SKSSWGLENEALIVRCPQRGRSTYPVEWYYSDTNESIPTQKRNRIFVSRDRLKF<br>LPARVEDSGIYACVIRSPNLNKTGYLNVTIHKKPPSCNIPDYLMYSTVRGSDKNF<br>KITCPTIDLYNWTAPVQWFKNCKALQEPRFRAHRSYLFIDNVTHDDEGDYTCQF<br>THAENGTNYIVTATRSFTVEEKGFSMFPVITNPPYNHTMEVEIGKPASIACSACF<br>GKGSHFLADVLWQINKTVVGNFGEARIQEEEGRNESSSNDMDCLTSVLRITGVT<br>EKDLSLEYDCLALNLHGMIRHTIRLRRKQPIDHR |
| SEQ ID NO: 7 (human ILIRAcP extracellular domain) | SERCDDWGLDTMRQIQVFEDEPARIKCPLFEHFLKFNYSTAHSAGLTLIWYWTR<br>QDRDLEEPINFRLPENRISKEKDVLWFRPTLLNDTGNYTCMLRNTTYCSKVAFPL<br>EVVQKDSCFNSPMKLPVHKLYIEYGIQRITCPNVDGYFPSSVKPTITWYMGCYKI<br>QNFNNVIPEGMNLSFLIALISNNGNYTCVVTYPENGRTFHLTRTLTVKVVGSPKN<br>AVPPVIHSPNDHVVYEKEPGEELLIPCTVYFSFLMDSRNEVWWTIDGKKPDDITI<br>DVTINESISHSRTEDETRTQILSIKKVTSEDLKRSYVCHARSAKGEVAKAAKVKQK<br>VPAPRYTVE |
| SEQ ID NO: 8 (mouse ILIRAcP extracellular domain) | SERCDDWGLDTMRQIQVFEDEPARIKCPLFEHFLKYNYSTAHSSGLTLIWYWTR<br>QDRDLEEPINFRLPENRISKEKDVLWFRPTLLNDTGNYTCMLRNTTYCSKVAFPL<br>EVVQKDSCFNSAMRFPVHKMYIEHGIHKITCPNVDGYFPSSVKPSVTWYKGCTE<br>IVDFHNVLPEGMNLSFFIPLVSNNGNYTCVVTYPENGRLFHLTRTVTVKVVGSPK<br>DALPPQIYSPNDRVVYEKEPGEELVIPCKVYFSFIMDSHNEVWWTIDGKKPDDV<br>TVDITINESVSYSSTEDETRTQILSIKKVTPEDLRRNYVCHARNTKGEAEQAAKVK<br>QKVIPPRYTVE |
| SEQ ID NO: 9 (human IgG1 Fc) | DKTHTCPPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKEYKCKVSNK<br>ALPAPIEKTISKAKGQPREPQVYTLPPSRDELTKNQVSLTCLVKGFYPSDIAVEW<br>ESNGQPENNYKTTPPVLDSDGSFFLYSKLTVDKSRWQQGNVFSCSVMHEALH<br>NHYTQKSLSLSPGK |

TABLE Ib-continued

Amino Acid Sequences

| Identifier | Sequence |
|---|---|
| SEQ ID NO: 10 (mouse IgG2a Fc) | EPRGPTIKPCPPCKCPAPNLLGGPSVFIFPPKIKDVLMISLSPIVTCVVVDVSEDD PDVQISWFVNNVEVHTAQTQTHREDYNSTLRVVSALPIQHQDWMSGKEFKCKV NNKDLPAPIERTISKPKGSVRAPQVYVLPPPEEEMTKKQVTLTCMVTDFMPEDIY VEWTNNGKTELNYKNTEPVLDSDGSYFMYSKLRVEKKNWVERNSYSCSVVHE GLHNHHTTKSFSRTPGK |
| SEQ ID NO: 11 (M. fascicularis IL-33-6H is) | SITGISPITESLASLSTYNDQSITFALEDESYEIYVEDLKKDKKKDKVLLSYYESQH PSSESGDGVDGKMLMVTLSPTKDFWLQANNKEHSVELHKCEKPLPDQAFFVLH NRSFNCVSFECKTDPGVFIGVKDNHLALIKVDYSENLGSENILFKLSEILEHHHHH H |
| SEQ ID NO: 13 (hST2-hiL1 RAcP-hFc) | KFSKQSWGLENEALIVRCPRQGKPSYTVDWYYSQTNKSIPTQERNRVFA SGQLLKFLPAAVADSGIYTCIVRSPTFNRTGYANVTIYKKQSDCNVPDYL MYSTVSGSEKNSKIYCPTIDLYNVVTAPLEWFKNCQALQGSRYRAHKSFL VIDNVMTEDAGDYTCKFIHNENGANYSVTATRSFTVKDEQGFSLFPVIGA PAQNEIKEVEIGKNANLTCSACFGKGTQFLAAVLWQLNGTKITDFGEPRI QQEEGQNQSFSNGLACLDMVLRIADVKEEDLLLQYDCLALNLHGLRRHT VRLSRKNPIDHHSSERCDDWGLDTMRQIQVFEDEPARIKCPLFEHFLKFN YSTAHSAGLTLIWYWTRQDRDLEEPINFRLPENRISKEKDVLWFRPTLLN DTGNYTCMLRNTTYCSKVAFPLEVVQKDSCFNSPMKLPVHKLYIEYGIQR ITCPNVDGYFPSSVKPTITWYMGCYKIQNFNNVIPEGMNLSFLIALISNNG NYTCVVTYPENGRTFHLTRTLTVKVVGSPKNAVPPVIHSPNDHVVYEKEP GEEELLIPCTVYFSFLMDSRNEVWWTIDGKKPDDITIDVTINESISHSRTEDE TRTQILSIKKVTSEDLKRSYVCHARSAKGEVAKAAKVKQKVPAPRYTVED KTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQ GNVFSCSVMHEALHNHYTQKSLSLSPGK |

Certain biological properties of the exemplary IL-33 antagonists generated in accordance with this Example are described in detail in the Examples set forth below.

Example 2. Binding of IL-33 Antagonists to Human, Mouse and Monkey IL-33 as Determined by Surface Plasmon Resonance Equilibrium dissociation constants ($K_D$ values) for human IL-33 (R&D Systems, #3625-IL-010/CF), mouse IL-33 (R&D Systems, #3626-ML-010/CF) and monkey IL-33 expressed with C-terminal hexahistidine tag (MfIL-33-6His; SEQ ID NO:12) binding to purified IL-33 Trap proteins and ST2 receptor proteins were determined using a real-time surface plasmon resonance biosensor using Biacore T-200 instrument at 25° C. and/or at 37° C. The Biacore sensor surface was first derivatized by amine coupling a polyclonal rabbit anti-mouse antibody (GE, # BR-1008-38) or with a monoclonal mouse anti-human Fc antibody (GE, # BR-1008-39) to capture IL-33 Trap and receptor proteins with a C-terminal mouse IgG2a Fc tag or a C-terminal human IgG1 Fc tag, respectively. Kinetic experiments were carried out in 0.01 M HEPES pH 7.4, 0.15 M NaCl, 3 mM EDTA, and 0.005% v/v Surfactant Tween-20 (HBST running buffer). Different concentrations of human IL-33, mouse IL-33 or MfIL-33-6His prepared in HBST running buffer (ranging from 60 nM to 27.4 pM, 3-fold dilutions, for Trap proteins and ranging from 60 nM to 0.25 nM, 3-fold dilutions, for ST2 receptor proteins) were injected over the captured IL-33 Trap and receptor protein surfaces at a flow rate of 50 μL/minute. Association of different IL-33 proteins to the different capture surfaces was monitored for 7 minutes for Trap proteins or 4 minutes for ST2 receptor proteins and their dissociation in HBST running buffer was monitored for 14 minutes for Trap proteins or 8 minutes for ST2 receptor proteins. Kinetic association ($k_a$) and dissociation ($k_d$) rate constants were determined by fitting the real-time binding sensorgrams to a 1:1 binding model using Scrubber 2.0c curve-fitting software. Binding dissociation equilibrium constants ($K_D$) and dissociative half-lives (t½) were calculated from the kinetic rate constants as:

$$K_D(M) = k_d/k_a \text{ and } t_{1/2} \text{ (min)} = \ln(2)/(60 * k_d)$$

The kinetic parameters for the IL-33 Trap proteins binding to human, monkey and mouse IL-33 at 25° C. and 37° C. are shown in Tables 2 through 7, while the binding kinetics for the ST2 receptor proteins binding to human and mouse IL-33 at 25° C. are shown in Tables 2 and 6. As shown in Table 2, the IL-33 Trap and receptor proteins bound human IL-33 with $K_D$ values ranging from approximately 0.53 pM to 54 pM at 25° C. As shown in Table 3, the IL-33 Trap proteins bound human IL-33 with $K_D$ values ranging from approximately 0.569 pM to 353 pM at 37° C. As shown in Table 4, the IL-33 Trap proteins bound MfIL-33-6HIs with $K_D$ values ranging from approximately 0.596 pM to 53.5 pM at 25° C. As shown in Table 5, the IL-33 Trap proteins bound MfIL-33-6HIs with $K_D$ values ranging from approximately 0.551 pM to 190 pM at 37° C. As shown in Table 6, the IL-33 Trap and receptor proteins bound mouse IL-33 with $K_D$ values ranging from approximately 6.1 pM to 102 pM at 25° C. As shown in Table 7, the IL-33 Trap proteins bound mouse IL-33 with $K_D$ values ranging from approximately 2.78 pM to 93.3 pM at 37° C.

TABLE 2

Binding kinetic parameters of human IL-33 binding to human IL-33 Trap, mouse IL-33 Trap, and human ST2 receptor proteins at 25° C.

| Captured Analyte | Amount of Analyte Captured (RU) | 60 nM Human IL-33 Bound (RU) | $k_a$ (1/Ms) | $k_d$ (1/s) | $K_D$ (M) | $t_{1/2}$ (min) |
|---|---|---|---|---|---|---|
| hST2-hIL1RAcP-hFc | 276 ± 0.7 | 19 | 1.89E+07 | 100E−05* | 5.30E−13* | 1155* |
| hST2-hIL1RAcP-mFc | 256 ± 2.9 | 28 | 1.92E+07 | 6.32E−05 | 3.29E−12 | 183 |
| mST2-mIL1RAcP-mFc | 233 ± 3.0 | 22 | 1.82E+07 | 1.29E−03 | 7.09E−11 | 9 |
| hST2-hFc | 230 ± 7.7 | 25 | 5.90E+06 | 3.20E−04 | 5.40E−11 | 36 |
| hST2-mFc | 255 ± 6.6 | 24 | 5.72E+06 | 3.07E−04 | 5.36E−11 | 38 |

*Under the experimental conditions, no dissociation of IL-33 from the captured monoclonal antibody was observed; therefore, the value of $k_d$ was fixed to 1.00E−05, and the derived $t_{1/2}$ and $K_D$ values represent lower and upper limits, respectively.

TABLE 3

Binding kinetics parameters of human IL-33 binding to human and mouse IL-33 Trap at 37° C.

| Captured Analyte | Amount of Analyte Captured (RU) | 60 nM Human IL-33 Bound (RU) | $k_a$ (1/Ms) | $k_d$ (1/s) | $K_D$ (M) | $t_{1/2}$ (min) |
|---|---|---|---|---|---|---|
| hST2-hIL1RAcP-hFc | 339 ± 10.7 | 26 | 1.76E+07 | 1.00E−05* | 5.69E−13* | 1155* |
| hST2-hIL1RAcP-mFc | 258 ± 4.3 | 28 | 1.82E+07 | 2.02E−05 | 1.11E−12 | 573 |
| mST2-mIL1RAcP-mFc | 222 ± 5.2 | 20 | 9.11E+06 | 3.22E−03 | 3.53E−10 | 4 |

*Under the experimental conditions, no dissociation of IL-33 from the captured monoclonal antibody was observed; therefore, the value of $k_d$ was fixed to 1.00E−05, and the derived $t_{1/2}$ and $K_D$ values represent lower and upper limits, respectively.

TABLE 4

Binding kinetic parameters of monkey IL-33 binding to human and mouse IL-33 Trap at 25° C.

| Captured Analyte | Amount of Analyte Captured (RU) | 60 nM Monkey IL-33 Bound (RU) | $k_a$ (1/Ms) | $k_d$ (1/s) | $K_D$ (M) | $t_{1/2}$ (min) |
|---|---|---|---|---|---|---|
| hST2-hIL1RACP-hFc | 274 ± 0.9 | 20 | 1.68E+07 | 1.00E−05* | 5.96E−13* | 1155* |
| hST2-hIL1RACP-mFc | 247 ± 4.1 | 28 | 1.31E+07 | 4.09E−05 | 3.13E−12 | 282 |
| mST2-mIL1RAcP-mFC | 225 ± 3.6 | 23 | 4.55E+06 | 2.44E−04 | 5.35E−11 | 47 |

*Under the experimental conditions, no dissociation of IL-33 from the captured monoclonal antibody was observed; therefore, the value of $k_d$ was fixed to 1.00E−05, and the derived $t_{1/2}$ and $K_D$ values represent lower and upper limits, respectively.

TABLE 5

Binding kinetic parameters of monkey IL-33 binding to human and mouse IL-33 Trap at 37° C.

| Captured Analyte | Amount of Analyte Captured (RU) | 60 nM Monkey IL-33 Bound (RU) | $k_a$ (1/Ms) | $k_d$ (1/s) | $K_D$ (M) | $t_{1/2}$ (min) |
|---|---|---|---|---|---|---|
| hST2-hIL1RAcP-hFc | 308 ± 8.2 | 25 | 1.82E+07 | 1.00E−05* | 5.51E−13* | 1155* |
| hST2-hIL1RAcP-mFc | 247 ± 3 | 27 | 1.45E+07 | 4.79E−05 | 3.29E−12 | 241 |
| mST2-mIL1RAcP-mFc | 209 ± 3.1 | 21 | 6.16E+06 | 1.17E−03 | 1.90E−10 | 10 |

*Under the experimental conditions, no dissociation of IL-33 from the captured monoclonal antibody was observed; therefore, the value of $k_d$ was fixed to 1.00E−05, and the derived $t_{1/2}$ and $K_D$ values represent lower and upper limits, respectively.

TABLE 6

Binding kinetic parameters of mouse IL-33 binding to human IL-33 Trap, mouse IL-33 Trap, and human ST2 receptor proteins at 25° C.

| Captured Analyte | Amount of Analyte Captured (RU) | 60 nM Mouse IL-33 Bound (RU) | $k_a$ (1/Ms) | $k_d$ (1/s) | $K_D$ (M) | $t_{1/2}$ (min) |
|---|---|---|---|---|---|---|
| hST2-hIL1RAcP-hFc | 272 ± 0.9 | 17 | 3.66E+06 | 2.23E−05 | 6.10E−12 | 517 |
| hST2-hIL1RAcP-mFc | 237 ± 2.7 | 22 | 4.67E+06 | 8.97E−05 | 1.92E−11 | 129 |
| mST2-mIL1RAcP-mFc | 217 ± 1.9 | 22 | 4.73E+06 | 4.94E−05 | 1.05E−11 | 234 |
| hST2-hFc | 211 ± 4.4 | 18 | 4.10E+06 | 4.23E−04 | 1.02E−10 | 27 |
| hST2-mFc | 238 ± 4.1 | 18 | 3.97E+06 | 3.50E−04 | 8.82E−11 | 33 |

TABLE 7

Binding kinetic parameters of mouse IL-33 binding to human and mouse IL-33 Trap at 37° C.

| Captured Analyte | Amount of Analyte Captured (RU) | 60 nM Mouse IL-33 Bound (RU) | $k_a$ (1/Ms) | $k_d$ (1/s) | $K_D$ (M) | $t_{1/2}$ (min) |
|---|---|---|---|---|---|---|
| hST2-hIL1RAcP-hFc | 280 ± 7.7 | 18 | 3.60E+06 | 1.00E−05* | 2.78E−12* | 1155* |
| hST2-hIL1RAcP-mFc | 236 ± 3.2 | 21 | 3.39E+06 | 3.17E−04 | 9.33E−11 | 36 |
| mST2-mIL1RAcP-mFc | 199 ± 2.8 | 20 | 6.00E+06 | 1.28E−04 | 2.13E−11 | 90 |

*Under the experimental conditions, no dissociation of IL-33 from the captured monoclonal antibody was observed; therefore, the value of $k_d$ was fixed to 1.00E−05, and the derived $t_{1/2}$ and $K_D$ values represent lower and upper limits, respectively.

Example 3. IL-33 Antagonists Block Binding of IL-33 to the Human ST2 Receptor The ability of exemplary IL-33 antagonists of the invention to block human IL-33 (hIL-33) binding to the human ST2 receptor was measured using a competition sandwich ELISA. A portion of human ST2 protein ecto domain that was expressed with a C-terminal mouse Fc tag (SEQ ID NO:2) was coated at a concentration of 1 µg/mL in PBS buffer on a 96-well microtiter plate overnight at 4° C. Nonspecific binding sites were subsequently blocked with a 0.5% (w/v) BSA solution in PBS. Biotinylated hIL-33 protein (R&D systems, #3625-IL/CF) (biot-hIL-33) was added to achieve a constant final concentration of 20 pM to serial dilutions of IL-33 antagonists ranging from 0 to 100 nM. The mixture was incubated for 1 hour at room temperature (RT) before transfer to the hST2-hFc coated microtiter plates. After incubation for 1 hour at RT, the wells were then washed, and plate-bound biot-hIL-33 was detected with HRP-conjugated streptavidin (Thermo Scientific, # N200). All samples were developed with a TMB solution (BD biosciences, #51-2607KC) to produce a colorimetric reaction and then quenched by acidification with 1M sulfuric acid before measuring absorbance at 450 nm on a Victor X5 plate reader (PerkinElmer). Data analysis was performed using a sigmoidal dose-response model within Prism™ software. The calculated $IC_{50}$ value, defined as the concentration of antagonist molecule required to block 50% of biot-hIL-33 binding to hST2-mFc, was used as an indicator of blocking potency. Maximum blocking values represent the ability of the antagonists to block IL-33 binding relative to baseline. The absorbance measured at the constant amount of hIL-33 on the dose curve was defined as 0% blocking and the absorbance with no added IL-33 was defined as 100% blocking. The absorbance values of the wells containing the highest concentration tested for each antagonist were used to determine the maximum blocking percent.

TABLE 8

ELISA Blocking of Biotin-hIL-33 to hST2-hFc by IL-33 Antagonists

| IL-33 Antagonist | Blocking 20 pM biotin-hIL-33 on hST2-hFc, $IC_{50}$ (M) | % Maximum blocking |
|---|---|---|
| hST2-hFc | 1.92E−11 | 99 |
| hST2-mFc | 1.69E−11 | 100 |
| hST2-hIL1RAcP-mFc | 6.34E−12 | 97 |
| mST2-mIL1RAcP-mFc | 1.12E−10 | 97 |

The four IL-33 antagonists tested blocked biotin-hIL-33 binding to hST2-mFc with $IC_{50}$ values ranging from 112 pM to 6.34 pM with maximum blocking percent ranging from 97% to 100%, as shown in Table 8.

Example 4. Inhibition of IL-33-Mediated Receptor Signaling by IL-33 Antagonists

Interleukin-33 (IL-33) is a ligand for ST2, a toll-like/interleukin-1 receptor super-family member that associates with an accessory protein, IL-1RAcP (for review, see Kakkar and Lee, (2008), Nat Rev Drug Discovery, October; 7(10): 827-840). Upon activation of ST2/IL-1RAcP by IL-33, a signaling cascade is triggered through downstream molecules such as MyD88 (myeloid differentiation factor 88) and TRAF6 (TNF receptor associated factor 6), leading to activation of NFκB (nuclear factor-κB) among others. To develop a biologically relevant bioassay system to test IL-33 antagonists, human embryonic kidney cells (HEK293) were stably transfected to express human ST2 (amino acids 1-556 of accession number NP_057316) along with a luciferase reporter [NFκB response element (5×)-luciferase-IRES-GFP] (HEK293/hST2/NFkB-luciferase cell line). The HEK293 cell line expresses IL-1RAcP endogenously, and NFκB activation by IL-33 in HEK293 cells has been shown previously (Schmitz et al., (2005), Immunity 23:479-490). The stable cell line was isolated and maintained in 10% FBS, DMEM, NEAA, penicillin/streptomycin, and G418.

For the bioassay, HEK293/hST2/NFκB-luciferase cells were seeded onto 96-well assay plates at 10,000 cells per well in low serum media containing 0.1% FBS and OPTIMEM (Invitrogen, #31985-070) and then incubated at 37° C. in 5% $CO_2$ overnight. The next day, to determine the dose response of IL-33, either human IL-33 (hIL-33; R&D Systems, #3625-IL), cynomolgus monkey IL-33 expressed with a C-terminal hexahistidine tag (MfIL-33-6His; SEQ ID:11), or mouse IL33 (mIL-33; R&D Systems, #3626-IL) were serially diluted at 1:3 (hIL33: 15 nM-0.3 pM or 10 nM-0.2 pM, mfIL33: 1.5 nM-0.03 pM or 1 nM-0.05 pM, mIL33: 15 nM-0.3 pM or 10 nM-0.2 pM) and added to the cells. A control containing dilution buffer but no IL-33 was also added to one sample of cells. To measure inhibition, IL-33 Trap and soluble receptor proteins were serially diluted and added to the cells followed by addition of constant concentrations of IL-33 (5 pM or 20 pM for hIL-33, 5 pM or 3 pM for MfIL-33-6His and 30 pM for mIL-33). The dilution series of the soluble receptor and Traps before adding to cells was 1:3, starting at ~15, 150, 100, or 200 nM and ranging down to ~0.3, 3, or 2 pM, plus a control sample containing no Trap or soluble receptor protein control. A human Fc protein (Control Protein) was also serially diluted at 1:3 ranging from 798 nM to 0.01 nM or 100 nM to 0.002 nM and tested with hIL-33, MfIL-33-6His, and mIL-33 in the same manner as the Trap and receptor proteins. Luciferase activity was measured after 5.5 hours of incubation at 37° C. in 5% $CO_2$ using a Victor X (Perkin Elmer) plate reader, and the results were analyzed using nonlinear regression (4-parameter logistics) with Prism 5 software. Results are shown in Table 9.

TABLE 9

Inhibition of human IL-33, monkey IL-33, and mouse IL-33 activation of HEK293/hST2/NFkB-luciferase cells by IL-33 Trap proteins and soluble human ST2 receptor

| IL-33 | Human | Monkey | Mouse | Human | Monkey | Mouse |
|---|---|---|---|---|---|---|
| $EC_{50}$ (M) | 1.9E−12 | 1.7E−12 | 1.0E−11 | 2.5E−11 | 1.3E−12 | 8.8E−11 |
| Constant IL33 | 5 pM | 5 pM | 30 pM | 20 pM | 3 pM | 30 pM |
| Description | $IC_{50}$ (M) | $IC_{50}$ (M) | $IC_{50}$ (M) | $IC_{50}$ (M) | $IC_{50}$ (M) | $IC_{50}$ (M) |
| mST2-mIL1RAcP-mFc | 4.8E−10 | 6.4E−11 | 8.7E−12 | Not Tested | Not Tested | Not Tested |
| hST2-hIL1RAcP-mFc | 1.3E−12 | 1.3E−12 | 1.3E−11 | 1.3E−11 | 4.7E−11 | 1.9E−10 |
| hST2-hIL1RAcP-hFc | Not Tested | Not Tested | Not Tested | 3.0E−11 | 1.0E−10 | 3.7E−10 |

TABLE 9-continued

Inhibition of human IL-33, monkey IL-33, and mouse IL-33 activation of HEK293/hST2/NFkB-luciferase cells by IL-33 Trap proteins and soluble human ST2 receptor

| IL-33 | Human | Monkey | Mouse | Human | Monkey | Mouse |
|---|---|---|---|---|---|---|
| hST2-mFc | 1.2E−11 | 5.5E−12 | 1.4E−10 | Not Tested | Not Tested | Not Tested |
| hST2-hFc | 1.0E−11 | 4.6E−12 | 1.1E−10 | Not Tested | Not Tested | Not Tested |
| Control Protein | NB | NB | NB | NB | NB | NB |

NB = non-blocker

As shown in Table 9, all five of the tested IL-33 antagonists potently blocked ($IC_{50}$<1 nM) stimulation of human, cynomolgus monkey, and mouse IL-33 in this cell-based assay.

Example 5. An IL-33 Antagonist Inhibits IL-33-Mediated Basophil Activation

To further assess the in vitro characteristics of the IL-33 antagonists hST2-hIL1RAcP-mFc and hST2-hIL1RAcP-hFc, their ability to block IL-33-induced basophil activation was measured.

Peripheral blood mononuclear cells (PBMC) were purified from fresh whole blood from four different human donors by density gradient centrifugation. K2 EDTA whole blood was diluted 1:1 in RPMI 1640, carefully layered over Ficoll-Paque (GE Healthcare, #17-1440-03) and centrifuged to separate PBMC. The interphase layer containing the PBMC was aspirated, transferred to a new tube, and washed twice with MACS buffer that was comprised of a 1:20 dilution of the MACS BSA solution (Militenyi Biotec, #130-091-376) in MACS rinsing solution (Militenyi Biotec, #130-091-222). The purified PBMC were then plated (100 µL per well) in a v-bottom, polypropylene 96-well plate at a final concentration of ~3.0×10⁶ cells/mL in MACS buffer. To prime the basophils contained within the PBMC population, 1 ng of IL-3 (Sigma, # H7166-10UG) in 50 µL Dulbecco's Phosphate-Buffered Saline without $Ca^{++}$ or $Mg^{++}$ (DPBS) was added to the cell suspension, and then incubated at 37° C. for 10 minutes. Serial dilutions (1:3 for donors 655675 and 655676 and 1:4 for donors 655685, 655686, 698846 and 698847) of the human IL-33 antagonists (hST2-hIL1RAcP-mFc or hST2-hIL1RAcP-hFc) or an irrelevant control protein were made, ranging from 10 nM to 4.6 pM for donors 655675 and 655676 and from 5 nM to 0.3 pM for donors 655685, 655686, 698846 and 698847. Additionally, a control with no IL-33 antagonist or irrelevant control protein was included. The solutions were mixed with a fixed concentration of 100 pM (final concentration) of human IL-33 (R&D Systems, #6325-IL/CF) or no IL-33 negative control prior to adding to the PBMC. All samples were tested in duplicate.

After addition of the human IL-33 and the human IL-33 antagonist to the cells, they were incubated at 37° C. for 20 minutes to facilitate basophil activation. Activation was then stopped by cooling the assay plates on wet ice for 5 minutes. To enable analysis of the basophil population used to measure activation, 20 µL each (as per the manufacturer's instructions) of anti-HLA-DR-FITC (Beckman Coulter, # IM0463U), anti-CD123-APC (BD, #560087), and anti-CD203c-PE (Beckman Coulter, #1M3575) were added to each sample, and the samples were held at 4° C. for 20 minutes in the dark. The cells were then centrifuged, washed with DPBS, and then resuspended in 2% formaldehyde (fixation buffer) at 4° C. The next day, fixed cells were analyzed on a BD FACSCanto II to determine levels of basophil activation. Basophils are identified according the following flow cytometric parameters: lymphocyte gate/$CD123^+$/$HLA-DR2^-$. Basophil activation is defined as an increase in the cell surface expression marker, CD203c on stimulated basophils. Activation is defined as frequency of CD203c positive basophils (%). Results are summarized in Tables 10 and 11 ("NB"=non-blocking; "ND"=not determined in the individual experiments). Data are shown as mean of 3 biological replicates for each donor.

TABLE 10

Percent Activation of Human Basophils Induced by Human IL-33 Challenge

| | 100 pM IL-33 | | No IL-33 | |
|---|---|---|---|---|
| Donor | Mean | SD | Mean | SD |
| 655675 | 39.00 | 0.28 | 9.43 | 0.02 |
| 655676 | 29.75 | 0.21 | 9.36 | 2.18 |
| 655685 | 42.30 | 3.39 | 10.9 | 0.42 |
| 655686 | 52.60 | 2.69 | 10.59 | 0.86 |
| 698846 | 26.25 | 0.78 | 9.79 | 0.18 |
| 698847 | 22.10 | 1.98 | 8.83 | 0.44 |

TABLE 11

Blocking of IL-33 Induced Activation of Human Basophil by IL-33 Antagonist

| Antagonist | Donor 655675 $IC_{50}$ (M) | Donor 655676 $IC_{50}$ (M) | Donor 655685 $IC_{50}$ (M) | Donor 655686 $IC_{50}$ (M) | Donor 698846 $IC_{50}$ (M) | Donor 698847 $IC_{50}$ (M) |
|---|---|---|---|---|---|---|
| hST2-hIL1RAcP-mFc | 1.90E−11 | 1.51E−11 | 2.30E−11 | 2.09E−11 | 3.60E−11 | 1.11E−11 |
| hST2-hIL1RAcP-hFc | ND | ND | ND | ND | 1.97E−11 | 9.79E−12 |
| Irrelevant control protein | NB | NB | NB | NB | NB | NB |

As shown in Table 10, at 100 pM, human IL-33 induced basophil activation in six different donors with a mean percent activation ranging from 22.1% to 52.60%.

As shown in Table 11, the IL-33 antagonist hST2-hIL1RAcP-mFc blocked basophil activation induced by 100 pM human IL-33 challenge with an $IC_{50}$ value of 19 pM for donor 655675, an $IC_{50}$ value of 15.1 pM for donor 655676, an $IC_{50}$ value of 23 pM for donor 655685, an $IC_{50}$ value of 20.9 pM for donor 655686, an $IC_{50}$ value of 36 pM for donor 698846 and an $IC_{50}$ value of 11.1 pM for donor 698847. The IL-33 antagonist hST2-hIL1RAcP-hFc blocked basophil activation induced by 100 pM human IL-33 challenge with an $IC_{50}$ value of 19.7 pM for donor 698846 and an $IC_{50}$ value of 9.79 pM for donor 698847. The irrelevant control protein did not block basophil activation from any of the tested donors.

Example 6. An IL-33 Antagonist Inhibits IL-33-Mediated Cell Activation

To further test the blocking properties of the human IL-33 antagonists hST2-hl L1RAcP-mFc and hST2-hIL1RAcP-hFc, a primary cell based assay using peripheral blood mononuclear cells (PBMCs) was used (see, e.g., Smithgall et al., *International Immunology*, 2008, vol. 20 (8) pp. 1019-1030).

PBMCs were purified from fresh whole human blood from six different donors by density gradient centrifugation. Briefly, K2 EDTA whole blood was diluted two-fold in RPMI 1640, carefully layered over Ficoll-Paque (GE Healthcare, #17-1440-03) and centrifuged for 20 minutes. The interphase layer containing the PBMCs was aspirated, transferred to a new tube, and washed twice with PBS. The isolated PBMCs were plated (200 μL per well) in round-bottom 96-well plates at a final concentration of $5 \times 10^5$ cells/mL in RPMI 1640 supplemented with 10% FBS, 2 mM L-glutamine, 100 U/mL penicillin, and 100 μg/mL streptomycin. Cells were then incubated with 50 ng/mL of human IL-12 (hIL-12; R&D Systems, #219-IL-025/CF) and a serial dilution of human IL-33 (hIL-33; R&D Systems, #3625-IL-010/CF) alone from 10 nM to 0.64 pM, or with 260 pM of hIL-33 in combination with serial dilutions from 20 nM to 0.43 pM of human IL-33 antagonist or an irrelevant mIgG containing control protein. The final volume was 200 μL per well. Each sample was tested in triplicate. When the IL-33 antagonist or irrelevant mIgG containing control protein was present, it was first pre-incubated with hIL-33 for 30 minutes and then added to the cells.

The cells were incubated overnight at 37° C. in a humidified incubator with 5% $CO_2$, and then IFNγ levels in the culture supernatant were measured by ELISA (R&D Systems, #DY285). For the ELISA, 96-well flat-bottom plates were coated with the capture antibody, according to the manufacturer's instructions. After washing and blocking, 100 μL of undiluted culture supernatant was added to the plates and incubated for 2 hours. Subsequent washes and detection were done following the manufacturer's instructions. Results are summarized in Tables 12 and 13 ("NB"=non-blocking, "ND"=not determined).

TABLE 12

IL-33 Induced IFNγ Release From Human PBMC from four Donors.

| [IL-33] | Donor 698843 | Donor 698842 | Donor 655684 | Donor 634966 | Donor 655681 | Donor 655682 | Donor 727054 | Donor 727055 |
|---|---|---|---|---|---|---|---|---|
| $EC_{50}$ (M) | ND | ND | 2.11E−10 | 3.15E−10 | 2.04E−10 | 3.04E−10 | ND | ND |

TABLE 13

Blocking of IL-33 Induced IFN-γ Release from Human PBMC by IL-33 Antagonist

| Antagonist | Donor 698843 $IC_{50}$ (M) | Donor 698842 $IC_{50}$ (M) | Donor 655684 $IC_{50}$ (M) | Donor 634966 $IC_{50}$ (M) | Donor 655681 $IC_{50}$ (M) | Donor 655682 $IC_{50}$ (M) | Donor 727054 $IC_{50}$ (M) | Donor 727055 $IC_{50}$ (M) |
|---|---|---|---|---|---|---|---|---|
| hST2-hIL1RAcP-mFc | 1.73E−11 | 7.39E−11 | 6.79E−11 | 2.13E−12 | 4.59E−11 | 3.97E−12 | 3.34E−10 | 1.23E−10 |
| hST2-hIL1RAcP-hFc | ND | ND | ND | ND | ND | ND | 1.52E−10 | 4.07E−10 |
| Irrelevant mIgG containing control protein | NB | NB | NB | NB | NB | NB | NB | NB |

As shown in this Example, Human IL-33, in the presence of hIL-12, induced the release of IFNγ from human total PBMC from the four different donors tested, with $EC_{50}$ values between 204 pM to 315 pM as shown in Table 12. The human IL-33 antagonist hST2-hIL1RAcP-mFc blocked the release of IFNγ from human PBMC induced by 260 pM IL-33, with $IC_{50}$ values ranging from 2.13 pM to 334 pM, as shown in Table 13. The irrelevant mIgG containing control protein did not demonstrate any measurable blockade of IFNγ release in any of the donors tested.

Example 7. Efficacy of mST2-mIL1RacP-mFc in a Model of Inflammatory Joint Pain To determine the effect of mST2-mIL1RacP-mFc in a relevant in vivo model a unilateral inflammatory joint pain model was conducted in 12 week old, male C57BL/6 mice obtained from The Jackson Laboratory (Bar Harbor, Me.). On day 0 of the experiment, separate cohorts of mice were subcutaneously administered either 50 mg/kg of mST2-mIL1RacP-mFc (n=15-16) or 50 mg/kg of an isotype control antibody (n=15-16). Twenty-four hours after the initial treatment dosing, half of the mice received a 30 μL intrarticular and a 50 μL periarticular injection of Complete Freund's Adjuvant (IA-CFA; Sigma, # F5881) (n=7-8) and the other half of the mice received control saline injections in the same locations (n=7-8). One week after the initiation of joint inflammation and continuing for the following four weeks, all mice received subcutaneous boost injections of 50 mg/kg of mST2-mIL1RacP-mFc or 50 mg/kg of an isotype control antibody 24 hours prior to testing in a dynamic weight-bearing assay (BioSeb, Vitrolles, FR). The percent of weight borne on the affected limb and the percent of time spent on the affected limb were recorded from all mice. The results of this experiment, expressed as the average percent of the total body weight or average percent time spent on the affected limb over the test period of 5 minutes, are shown in Table 14 and Table 15 (all data are represented as group mean±SEM). The cohorts of mice that received IA-CFA all displayed significantly less ($p<0.05$ by ANOVA) weight bearing on the affected limb. The mice that received mST2-mIL1RacP-mFc after IA-CFA administration demonstrated higher percent weight bearing and time spent on affected limb scores at all time points tested compared to the isotype control treated mice after IA-CFA administration as shown in Tables 14 and 15.

Following week four, all animals were euthanized and the affected joints were dissected, paraffin embedded, sectioned, and stained with hemotoxylin and eosin for histological analysis. Sections were digitized and scored in a blinded manner using a subjective rating scale of inflammatory activity (including joint destruction, synovial thickening, bone erosion, and immune cell infiltrate) graded from 0-5 (0=normal, 1=minimal, 2=mild, 3=moderate, 4=marked, 5=severe) following a method similar to that outlined in Choe et. al. (Choe, J Y et. al., (2003), J. Exp. Med. February 17; 197(4):537-542). As shown in Table 16, mice treated with mST2-mIL1RacP-mFc after IA-CFA administration demonstrated more "moderate" and less "severe" knee joints compared to the isotype control treated mice after IA-CFA administration. This example therefore indicates that the IL-33 antagonists of the invention are useful in alleviating inflammatory joint pain.

TABLE 14

Percent of body weight borne on affected limb

| Treatment | Week 1 | Week 2 | Week 3 | Week 4 |
| --- | --- | --- | --- | --- |
| Saline Control + Isotype control | 43.1 ± 1.6 | 42.2 ± 1.0 | 41.1 ± 1.7 | 41.1 ± 0.9 |
| Saline Control + mST2-mIL1RacP-mFc | 41.5 ± 1.9 | 43.3 ± 0.6 | 42.2 ± 1.2 | 38.7 ± 1.4 |
| IA-CFA + Isotype control | 24.9 ± 1.4 | 24.2 ± 1.5 | 23.8 ± 1.0 | 23.6 ± 2.0 |
| IA-CFA + mST2-mIL1RacP-mFc | 30.1 ± 2.1 | 24.4 ± 1.0 | 28.3 ± 2.6 | 29.8 ± 2.9 |

TABLE 15

Percent of time spent on affected limb

| Treatment | Week 1 | Week 2 | Week 3 | Week 4 |
| --- | --- | --- | --- | --- |
| Saline Control + Isotype control | 96.6 ± 1.0 | 96.6 ± 0.6 | 96.2 ± 0.9 | 96.4 ± 0.6 |
| Saline Control + mST2-mIL1RacP-mFc | 95.5 ± 0.8 | 97.2 ± 0.3 | 94.3 ± 1.7 | 97.0 ± 0.5 |
| IA-CFA + Isotype control | 68.4 ± 1.6 | 64.8 ± 2.1 | 72.8 ± 3.5 | 80.9 ± 2.7 |
| IA-CFA + mST2-mIL1RacP-mFc | 78.9 ± 3.6 | 68.5 ± 3.1 | 80.9 ± 4.2 | 88.0 ± 2.7 |

TABLE 16

Histological severity scores for affected knee joints (% of animals)

| Treatment | Minimal | Mild | Moderate | Severe |
| --- | --- | --- | --- | --- |
| IA-CFA + Isotype control | 0 | 0 | 12% | 88% |
| IA-CFA + mST2-mIL1RacP-mFc | 0 | 0 | 38% | 62% |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of treating an inflammatory disease or disorder, or at least one symptom associated with the inflammatory disease or disorder, the method comprising administering, to a patient in need thereof, an interleukin-33 (IL-33) antagonist comprising a first IL-33 binding domain (D1), a second IL-33 binding domain (D2), and a multimerizing domain (M), wherein D1, or D2, or both D1 and D2 are attached to the multimerizing domain (M), wherein D1 comprises an extracellular portion of a human suppression of tumorigenicity (ST2) protein, D2 comprises an extracellular portion of a human interleukin-1 receptor accessory protein (IL-1RAcP), and M comprises an Fc portion of an immunoglobulin, wherein the inflammatory disease or disorder is alleviated, or reduced in severity, duration or frequency of occurrence, or at least one symptom associated with the inflammatory disease or disorder is alleviated, or reduced in severity, duration, or frequency of occurrence.

2. The method of claim 1, wherein the inflammatory disease or disorder is selected from the group consisting of asthma, atopic dermatitis, chronic obstructive pulmonary disease (COPD), inflammatory bowel disease, multiple sclerosis, arthritis, allergic rhinitis, eosinophilic esophagitis and psoriasis.

3. The method of claim 2, wherein the inflammatory disease or disorder is asthma.

4. The method of claim 3, wherein the asthma is eosinophilic or non-eosinophilic asthma.

5. The method of claim 2, wherein the asthma is steroid resistant or steroid sensitive asthma.

6. The method of claim 1, wherein the inflammatory disease or disorder is atopic dermatitis.

7. The method of claim 1, wherein the inflammatory disease or disorder is chronic obstructive pulmonary disease (COPD).

8. The method of claim 7, wherein the chronic obstructive pulmonary disease results from, or is caused in part by cigarette smoke.

9. The method of claim 1, further comprising administering an effective amount of a second therapeutic agent useful for alleviating the inflammatory disease or disorder, or at least one symptom of the inflammatory disease or disorder, or for diminishing an allergic response to an allergen.

10. The method of claim 9, wherein the second therapeutic agent is selected from the group consisting of a non-steroidal anti-inflammatory (NSAID), a corticosteroid, a bronchial dilator, an antihistamine, epinephrine, a decongestant, a thymic stromal lymphopoietin (TSLP) antagonist, an IL-13 antagonist, an IL-4 antagonist, an IL-4/IL-13 dual antagonist, an IL-5 antagonist, an IL-6 antagonist, an IL-12/23 antagonist, an IL-22 antagonist, an IL-25 antagonist, an IL-17 antagonist, an IL-31 antagonist, an oral PDE4 inhibitor, another IL-33 antagonist, and an antibody to IL-33.

11. The method of claim 1, wherein D2 is attached to the N-terminus of D1, and wherein D1 is attached to the N-terminus of M.

12. The method of claim 1, wherein D1 is attached to the N-terminus of M, and D2 is attached to the C-terminus of M.

13. The method of claim 1, wherein D2 is attached to the N-terminus of M, and D1 is attached to the C-terminus of M.

14. The method of claim 1, wherein D1 is attached to the C-terminus of M, and D2 is attached to the C-terminus of D1.

15. The method of claim 1, wherein D2 is attached to the C-terminus of M, and D1 is attached to the C-terminus of D2.

16. The method of claim 1, wherein D1 is attached to the N-terminus of D2, and wherein D2 is attached to the N-terminus of M.

17. The method of claim 1, wherein the IL-33 antagonist binds human interleukin 33 (IL-33) with a binding dissociation equilibrium constant (KD) of less than about 80 pM as measured in a surface plasmon resonance assay at 25° C., and/or a binding dissociation equilibrium constant (KD) of less than about 400 pM as measured in a surface plasmon resonance assay at 37° C.

18. The method of claim 1, wherein the IL-33 antagonist binds monkey interleukin 33 (IL-33) with a binding dissociation equilibrium constant (KD) of less than about 60 pM as measured in a surface plasmon resonance assay at 25° C., and/or a binding dissociation equilibrium constant (KD) of less than about 200 pM as measured in a surface plasmon resonance assay at 37° C.

19. The method of claim 1, wherein the IL-33 antagonist binds mouse interleukin 33 (IL-33) with a binding dissociation equilibrium constant (KD) of less than about 110 pM as measured in a surface plasmon resonance assay at 25° C., and/or a binding dissociation equilibrium constant (KD) of less than about 100 pM as measured in a surface plasmon resonance assay at 37° C.

20. The method of claim 1, wherein the IL-33 antagonist binds human interleukin 33 (IL-33) with a dissociative half-life (t½) of greater than or equal to about 9 minutes as measured in a surface plasmon resonance assay at 25° C., and/or a dissociative half-life (t½) of greater than or equal to about 4 minutes as measured in a surface plasmon resonance assay at 37° C.

21. The method of claim 1, wherein the IL-33 antagonist binds monkey interleukin 33 (IL-33) with a dissociative half-life (t½) of greater than about 40 minutes as measured in a surface plasmon resonance assay at 25° C., and/or a dissociative half-life (t½) of greater than or equal to about 10 minutes as measured in a surface plasmon resonance assay at 37° C.

22. The method of claim 1, wherein the IL-33 antagonist binds mouse interleukin 33 (IL-33) with a dissociative half-life (t½) of greater than about 25 minutes as measured in a surface plasmon resonance assay at 25° C., and/or a dissociative half-life (t½) of greater than about 30 minutes as measured in a surface plasmon resonance assay at 37° C.

23. The method of claim 1, wherein the IL-33 antagonist blocks the interaction of IL-33 and ST2.

24. The method of claim 23, wherein the IL-33 antagonist blocks the interaction of IL-33 and ST2 with an IC50 value of less than about 115 pM as measured in an in vitro receptor/ligand binding assay at 25° C.

25. The method of claim 1, wherein D1 comprises the amino acid sequence of SEQ ID NO: 5, or an amino acid sequence having at least 90% identity thereto.

26. The method of claim 1, wherein D2 comprises the amino acid sequence of SEQ ID NO: 7, or an amino acid sequence having at least 90% identity thereto.

27. The method of claim 1, wherein the immunoglobulin is human IgG.

28. The method of claim 27, wherein the immunoglobulin is human IgG1.

29. The method of claim 1, wherein the immunoglobulin is murine IgG.

30. The method of claim 27, wherein the immunoglobulin is murine IgG2a.

31. The method of claim 1, wherein the IL-33 antagonist comprises the amino acid sequence of SEQ ID NO: 1.

32. The method of claim 1, wherein the IL-33 antagonist comprises the amino acid sequence of SEQ ID NO: 2.

33. The method of claim 1, wherein the IL-33 antagonist comprises the amino acid sequence of SEQ ID NO: 3.

34. The method of claim 1, wherein the IL-33 antagonist comprises the amino acid sequence of SEQ ID NO: 13.

35. A method of treating an inflammatory disease or disorder, or at least one symptom associated with the inflammatory disease or disorder, the method comprising administering, to a patient in need thereof, an interleukin-33 (IL-33) antagonist comprising a first IL-33 binding domain (D1), a second IL-33 binding domain (D2), and a multimerizing domain (M), wherein D1, or D2, or both D1 and D2 are attached to the multimerizing domain (M), wherein D1 comprises an extracellular portion of a suppression of tumorigenicity (ST2) protein, D2 comprises an extracellular portion of an interleukin-1 receptor accessory protein (IL-1RAcP), and M comprises an Fc portion of an immunoglobulin, wherein the inflammatory disease or disorder is alleviated, or reduced in severity, duration or frequency of occurrence, or at least one symptom associated with the inflammatory disease or disorder is alleviated, or reduced in severity, duration, or frequency of occurrence.

36. A method for treating a patient who demonstrates a sensitivity to an allergen, the method comprising administering, to a patient in need thereof, an interleukin-33 (IL-33) antagonist comprising a first IL-33 binding domain (D1), a second IL-33 binding domain (D2), and a multimerizing domain (M), wherein D1, or D2, or both D1 and D2 are attached to the multimerizing domain (M), wherein D1 comprises an extracellular portion of a human suppression of tumorigenicity (ST2) protein, D2 comprises an extracellular portion of a human interleukin-1 receptor accessory protein (IL-1RAcP), and M comprises an Fc portion of an immunoglobulin, wherein the patient demonstrates a reduced sensitivity to, or a diminished allergic reaction against the allergen, or does not experience any sensitivity or allergic reaction to, or anaphylactic response to the allergen following administration of the IL-33 antagonist.

* * * * *

UNITED STATES PATENT AND TRADEMARK OFFICE
CERTIFICATE OF CORRECTION

PATENT NO. : 10,011,647 B2
APPLICATION NO. : 15/463910
DATED : July 3, 2018
INVENTOR(S) : Andrew J. Murphy et al.

Page 1 of 1

It is certified that error appears in the above-identified patent and that said Letters Patent is hereby corrected as shown below:

In the Claims

Claim 30
Column 68, Line 32 "claim 27" should read --claim 29--

Signed and Sealed this
Eighteenth Day of September, 2018

Andrei Iancu
*Director of the United States Patent and Trademark Office*